US011981034B2

(12) United States Patent
Pinter et al.

(10) Patent No.: US 11,981,034 B2
(45) Date of Patent: May 14, 2024

(54) SOCIAL BEHAVIOR RULES FOR A MEDICAL TELEPRESENCE ROBOT

(71) Applicants: Teladoc Health, Inc., Purchase, NY (US); iRobot Corporation, Bedford, MA (US)

(72) Inventors: Marco Pinter, Goleta, CA (US); Fuji Lai, Goleta, CA (US); Daniel Steven Sanchez, Summerland, CA (US); James Ballantyne, Santa Barbara, CA (US); David Bjorn Roe, Santa Barbara, CA (US); Yulun Wang, Goleta, CA (US); Charles S. Jordan, Santa Barbara, CA (US); Orjeta Taka, Peabody, MA (US); Cheuk Wah Wong, Concord, MA (US)

(73) Assignees: TELADOC HEALTH, INC., Purchase, NY (US); IROBOT CORPORATION, Bedford, MA (US)

( * ) Notice: Subject to any disclaimer, the term of this patent is extended or adjusted under 35 U.S.C. 154(b) by 0 days.

(21) Appl. No.: 18/124,691

(22) Filed: Mar. 22, 2023

(65) Prior Publication Data
US 2023/0226694 A1 Jul. 20, 2023

Related U.S. Application Data

(63) Continuation of application No. 17/027,335, filed on Sep. 21, 2020, now Pat. No. 11,628,571, which is a
(Continued)

(51) Int. Cl.
*B25J 9/16* (2006.01)
*G06Q 50/22* (2018.01)
*G16H 40/67* (2018.01)

(52) U.S. Cl.
CPC ............ *B25J 9/1676* (2013.01); *G06Q 50/22* (2013.01); *G16H 40/67* (2018.01); *Y10S 901/01* (2013.01); *Y10S 901/47* (2013.01); *Y10S 901/49* (2013.01)

(58) Field of Classification Search
USPC .................................................. 700/245–264
See application file for complete search history.

(56) References Cited

U.S. PATENT DOCUMENTS 4,638,445 A * 1/1987 Mattaboni .............. B25J 9/0003
706/904
6,317,652 B1 * 11/2001 Osada .................... B25J 19/023
901/1
(Continued)

*Primary Examiner* — Jonathan L Sample
(74) *Attorney, Agent, or Firm* — Kory D. Christensen

(57) ABSTRACT

Devices, systems, and methods for social behavior of a telepresence robot are disclosed herein. A telepresence robot may include a drive system, a control system, an object detection system, and a social behaviors component. The drive system is configured to move the telepresence robot. The control system is configured to control the drive system to drive the telepresence robot around a work area. The object detection system is configured to detect a human in proximity to the telepresence robot. The social behaviors component is configured to provide instructions to the control system to cause the telepresence robot to operate according to a first set of rules when a presence of one or more humans is not detected and operate according to a second set of rules when the presence of one or more humans is detected.

14 Claims, 12 Drawing Sheets

Related U.S. Application Data continuation of application No. 16/418,605, filed on May 21, 2019, now Pat. No. 10,780,582, which is a continuation of application No. 15/720,214, filed on Sep. 29, 2017, now Pat. No. 10,328,576, which is a continuation of application No. 14/931,641, filed on Nov. 3, 2015, now Pat. No. 9,776,327, which is a continuation of application No. 14/550,743, filed on Nov. 21, 2014, now Pat. No. 9,174,342, which is a continuation of application No. PCT/US2013/031778, filed on Mar. 14, 2013.

(60) Provisional application No. 61/766,623, filed on Feb. 19, 2013, provisional application No. 61/674,794, filed on Jul. 23, 2012, provisional application No. 61/674,796, filed on Jul. 23, 2012, provisional application No. 61/674,782, filed on Jul. 23, 2012, provisional application No. 61/650,205, filed on May 22, 2012.

(56) References Cited

U.S. PATENT DOCUMENTS

| | | | | |
|---|---|---|---|---|
| 6,604,022 B2* | 8/2003 | Parker | | G06N 3/008 700/250 |
| 7,584,020 B2* | 9/2009 | Bruemmer | | G05D 1/024 701/25 |
| 7,587,260 B2* | 9/2009 | Bruemmer | | G06N 3/008 318/587 |
| 7,620,477 B2* | 11/2009 | Bruemmer | | G05D 1/0088 700/262 |
| 7,668,621 B2* | 2/2010 | Bruemmer | | G06N 3/008 318/568.22 |
| 7,801,644 B2* | 9/2010 | Bruemmer | | G06N 3/008 318/568.17 |
| 7,873,448 B2* | 1/2011 | Takeda | | G06T 7/20 701/28 |
| 7,974,738 B2* | 7/2011 | Bruemmer | | G05D 1/0088 318/568.18 |
| 8,073,564 B2* | 12/2011 | Bruemmer | | G05D 1/0027 700/245 |
| 8,077,963 B2* | 12/2011 | Wang | | G05D 1/0038 382/153 |
| 8,234,010 B2* | 7/2012 | Thompson | | G05D 1/0295 901/46 |
| 8,271,132 B2* | 9/2012 | Nielsen | | G05D 1/0088 700/250 |
| 8,355,818 B2* | 1/2013 | Nielsen | | G05D 1/0214 700/258 |
| 8,489,234 B2* | 7/2013 | Rew | | G05D 1/0255 700/258 |
| 8,632,376 B2* | 1/2014 | Dooley | | A63F 13/213 901/6 |
| 8,718,837 B2* | 5/2014 | Wang | | G16H 40/67 382/209 |
| 8,935,005 B2* | 1/2015 | Rosenstein | | G05D 1/0246 700/259 |
| 8,965,578 B2* | 2/2015 | Versteeg | | G05D 1/0088 700/258 |
| 9,323,250 B2* | 4/2016 | Wang | | G05D 1/0011 |
| 9,776,327 B2* | 10/2017 | Pinter | | G05D 1/0088 |
| 9,902,069 B2* | 2/2018 | Farlow | | G05D 1/0274 |
| 10,328,576 B2* | 6/2019 | Pinter | | G06Q 50/22 |
| 10,780,582 B2* | 9/2020 | Pinter | | G06Q 50/22 |
| 2002/0013641 A1* | 1/2002 | Nourbakhsh | | G06N 3/008 701/410 |
| 2002/0198626 A1* | 12/2002 | Imai | | G06N 3/008 700/245 |
| 2003/0016726 A1* | 1/2003 | Pavlidis | | A61B 5/164 374/45 |
| 2004/0140404 A1* | 7/2004 | Ohta | | B64C 39/024 244/190 |
| 2007/0016328 A1* | 1/2007 | Ziegler | | A47L 11/4088 318/609 |
| 2007/0156286 A1* | 7/2007 | Yamauchi | | G05D 1/027 700/245 |
| 2007/0192910 A1* | 8/2007 | Vu | | G05D 1/0246 901/1 |
| 2007/0198128 A1* | 8/2007 | Ziegler | | B25J 19/0091 713/153 |
| 2007/0234492 A1* | 10/2007 | Svendsen | | B60L 50/52 15/49.1 |
| 2007/0255115 A1* | 11/2007 | Anglin, Jr. | | G16H 10/60 600/300 |
| 2008/0086236 A1* | 4/2008 | Saito | | G01S 5/02524 901/1 |
| 2008/0316368 A1* | 12/2008 | Fritsch | | H04N 5/272 348/E5.022 |
| 2009/0030552 A1* | 1/2009 | Nakadai | | G10L 21/028 704/275 |
| 2009/0055019 A1* | 2/2009 | Stiehl | | B25J 9/1671 901/17 |
| 2009/0210090 A1* | 8/2009 | Takemitsu | | B25J 9/1661 901/1 |
| 2010/0030378 A1* | 2/2010 | Choi | | G01S 1/54 901/1 |
| 2010/0037418 A1* | 2/2010 | Hussey | | A47L 9/2894 901/1 |
| 2010/0063636 A1* | 3/2010 | Matsumoto | | F24F 11/63 700/276 |
| 2010/0153317 A1* | 6/2010 | Lee | | B25J 9/1661 901/50 |
| 2010/0243344 A1* | 9/2010 | Wyrobek | | B25J 19/0016 180/21 |
| 2011/0071672 A1* | 3/2011 | Sanders | | B25J 9/161 700/245 |
| 2011/0231050 A1* | 9/2011 | Goulding | | G05D 1/0891 180/8.1 |
| 2012/0182392 A1* | 7/2012 | Kearns | | B25J 13/08 348/46 |
| 2012/0185095 A1* | 7/2012 | Rosenstein | | G05D 1/0251 901/1 |
| 2013/0035790 A1* | 2/2013 | Olivier, III | | G06V 40/161 901/1 |
| 2013/0166137 A1* | 6/2013 | Ahn | | G05D 1/0272 701/32.3 |
| 2014/0254896 A1* | 9/2014 | Zhou | | G07F 17/13 705/16 |
| 2014/0302931 A1* | 10/2014 | Conceicao | | A63F 13/20 463/31 |
| 2016/0167231 A1* | 6/2016 | Nakayama | | B25J 9/1694 700/255 |
| 2016/0358276 A1* | 12/2016 | Stephenson | | G16H 20/00 |
| 2017/0106738 A1* | 4/2017 | Gillett | | B62K 5/08 |
| 2017/0144299 A1* | 5/2017 | Lafaye | | B25J 9/162 |

* cited by examiner

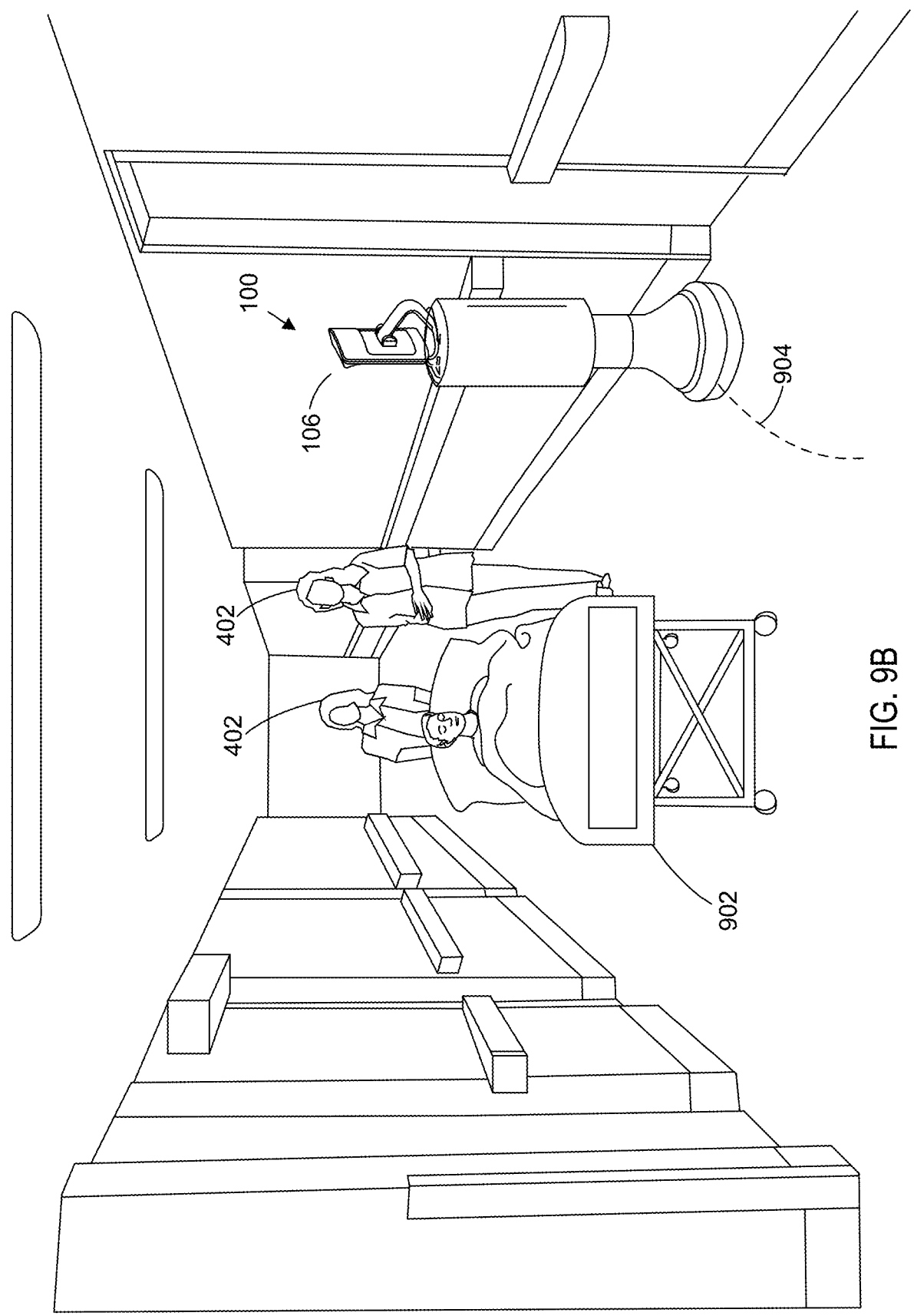

SOCIAL BEHAVIOR RULES FOR A MEDICAL TELEPRESENCE ROBOT

RELATED APPLICATIONS

This application is a continuation of U.S. patent application Ser. No. 17/027,335, filed Sep. 21, 2020, for "Social Behavior Rules for a Medical Telepresence Robot," which is a continuation of U.S. patent application Ser. No. 16/418,605, filed May 21, 2019, for "Social Behavior Rules for a Medical Telepresence Robot," which is a continuation of U.S. patent application Ser. No. 15/720,214, filed Sep. 29, 2017, for "Social Behavior Rules for a Medical Telepresence Robot," which is continuation of U.S. patent application Ser. No. 14/931,641, filed, Nov. 3, 2015, for "Social Behavior Rules for a Medical Telepresence Robot," which is a continuation of U.S. patent application Ser. No. 14/550,743, filed Nov. 21, 2014, for "Social Behavioral Rules for a Medical Telepresence Robot," now U.S. Pat. No. 9,174,342, which is a continuation of PCT Application No. PCT/US2013/031778, for "Social Behavioral Rules for a Medical Telepresence Robot," filed Mar. 14, 2013. The forgoing applications also claim priority under 35 U.S.C. § 119(e) to U.S. Provisional Application No. 61/650,205 filed May 22, 2012, titled "Remote Presence Interface and Patient Data Integration"; U.S. Provisional Application No. 61/674,794 filed Jul. 23, 2012, titled "Graphical User Interfaces Including Touchpad Driving Interfaces for Telemedicine Devices"; U.S. Provisional Application No. 61/674,796 filed Jul. 23, 2012, titled "Clinical Workflows Utilizing Autonomous and Semi-Autonomous Telemedicine Devices"; U.S. Provisional Application No. 61/674,782 filed Jul. 23, 2012, titled "Behavioral Rules For a Telemedicine Robot To Comply With Social Protocols"; and U.S. Provisional Application No. 61/766,623 filed Feb. 19, 2013, titled "Graphical User Interfaces Including Touchpad Driving Interfaces for Telemedicine Devices." All of the foregoing applications are all hereby incorporated by reference in their entireties.

TECHNICAL FIELD

This disclosure is generally related to behaviors and actions that can be executed by an autonomous or semi-autonomous robot to appear more human-like and/or comply with social protocols.

BRIEF DESCRIPTION OF THE DRAWINGS

FIG. 9B is a perspective view of a robot allowing the large group of FIG. 9A to pass with a head portion rotated.

DETAILED DESCRIPTION

In order to improve communication among hospital staff, healthcare professionals, patients, and other applicable parties in various locations, a robot may serve as a remote presence communication device. The robot may be capable of autonomous or semi-autonomous navigation through a healthcare facility with little or no manual intervention. The robot may drive in a manner such that it avoids both stationary and moving obstacles and people in its path.

In addition to avoiding contact with obstacles and people, the robot may move in harmony with social protocols and expectations. For example, this may include providing suitable space between itself and people, as well as moving in an unobtrusive manner so as not to alarm staff or visitors. Further, the robot may move fluidly within that context. The robot may also be capable of acting as a member of a group, enabling it to assist in group activities and procedures within a healthcare facility environment.

Disclosed herein are various embodiments of robots, robot behaviors, and methods for robots to achieve the various behaviors. According to various embodiments, the systems and methods disclosed herein may facilitate communication among medical professionals, staff, and patients. In addition, the systems and methods described herein facilitate the autonomous navigation of robots while engaging in human behaviors and obeying social protocols. For example, a doctor in a remote location may cause a robot to drive down a hallway to a patient's room. As the robot autonomously navigates to the patient's room, the robot may acknowledge and greet a human as it passes en route to a patient room.

Figure 1:
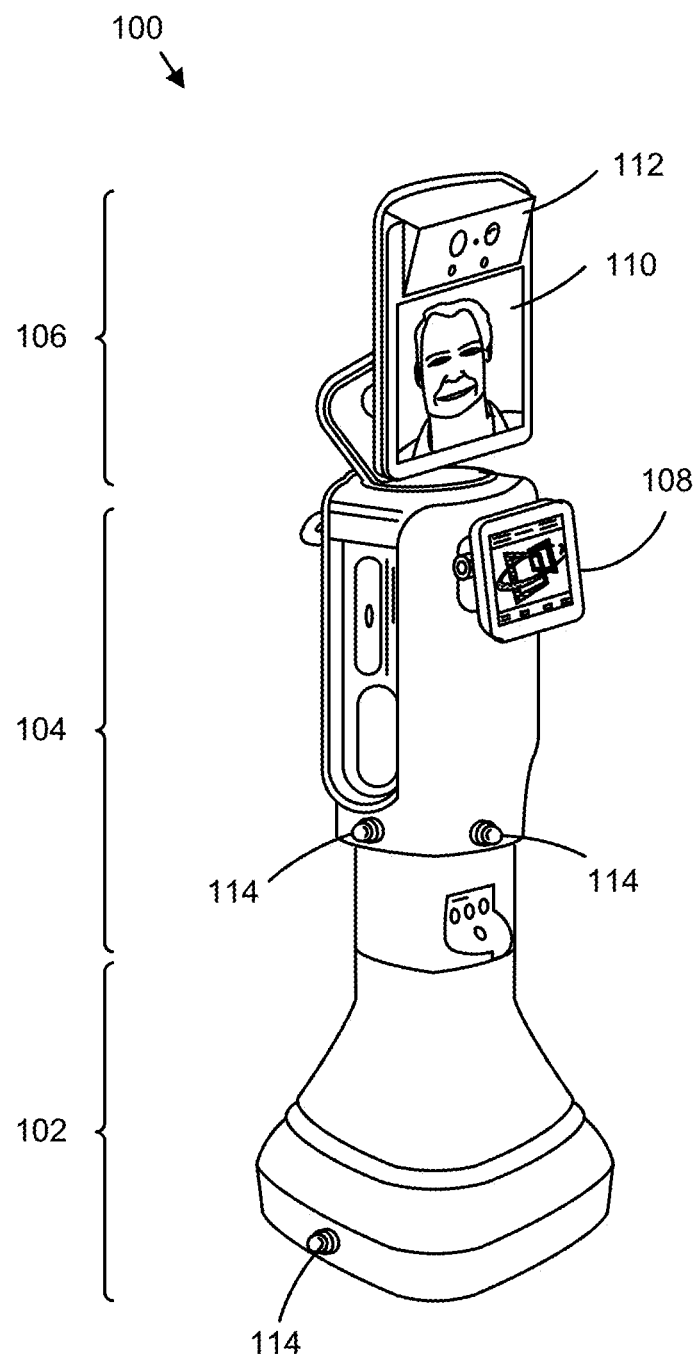
FIG. 1 is a perspective view of a medical telepresence robot.

FIG. 1 is a perspective view of a telepresence robot 100, according to one embodiment. The robot 100 includes a base 102, an upper portion 104, and a head 106. The robot 100 provides a variety of features and functions for allowing a user to remotely control the robot 100 and communicate with individuals on the site of the robot 100. For example, a doctor may be able to use the robot 100 to remotely communicate with a patient or coworker.

The base 102 supports the robot 100 and may include a drive system for moving the robot 100 about a work area. The base 102 may include any associated motors, batteries, wheels, or the like to move the robot 100. The upper portion 104 supports the head 106 and houses various component of the robot 100. The upper portion 104 may also provide various features and interfaces to allow a person to interface with the robot 100. For example, the upper portion 104 includes a display interface 108 that displays information about the robot 100 and/or allows a user to select different options to control the robot 100. Other ports, button, lights, or the like may be used to interface with the robot 100. In one embodiment, the upper portion 104 is configured to rotate independently of the base 102.

The head 106 represents a head of the robot 100 and includes a display screen 110 and a sensor housing 112. The display screen 110 may be used to selectively display video of a remote user, a caricature corresponding to a personality of the robot 100, or any other information. The display screen 110 may be configured to display a live video feed from a remote operator and/or a persona of the robot 100, itself. For example, the display screen 110 may display the face of a doctor remotely using the robot 100 for teleconsultations. When autonomously navigating, the robot 100 may have a personality portrayed through a caricature, face, icon, or other characteristic on the display screen 110.

The sensor housing 112 may house a variety of sensors such as microphones, cameras, range detector devices, or the like. For example, a video camera configured to capture a video feed of a point of view of the robot 100 may be captured and transmitted to a remote user. The video camera may also be used in conjunction with a range finding device, such as a laser range finder, to detect objects, humans, or other surrounding features that affect navigation of the robot 100. In one embodiment, the head 106 is able to rotate independently of the upper portion 104 and/or the base 102. In another embodiment, the head 106 is not rotatable with respect to the upper portion 104 and/or the base 102.

The robot 100 also includes lights 114 distributed on the surface of the robot 100. The lights 114 may be used to indicate a current status of the robot 100, reflect a personality of the robot 100, indicate an emergency, create a desired mood for a location within a work area, or indicate any other information to nearby humans. The robot 100 may also include additional lights, input devices, output devices, and/or a variety of other sensors that will be discussed below.

Figure 2:
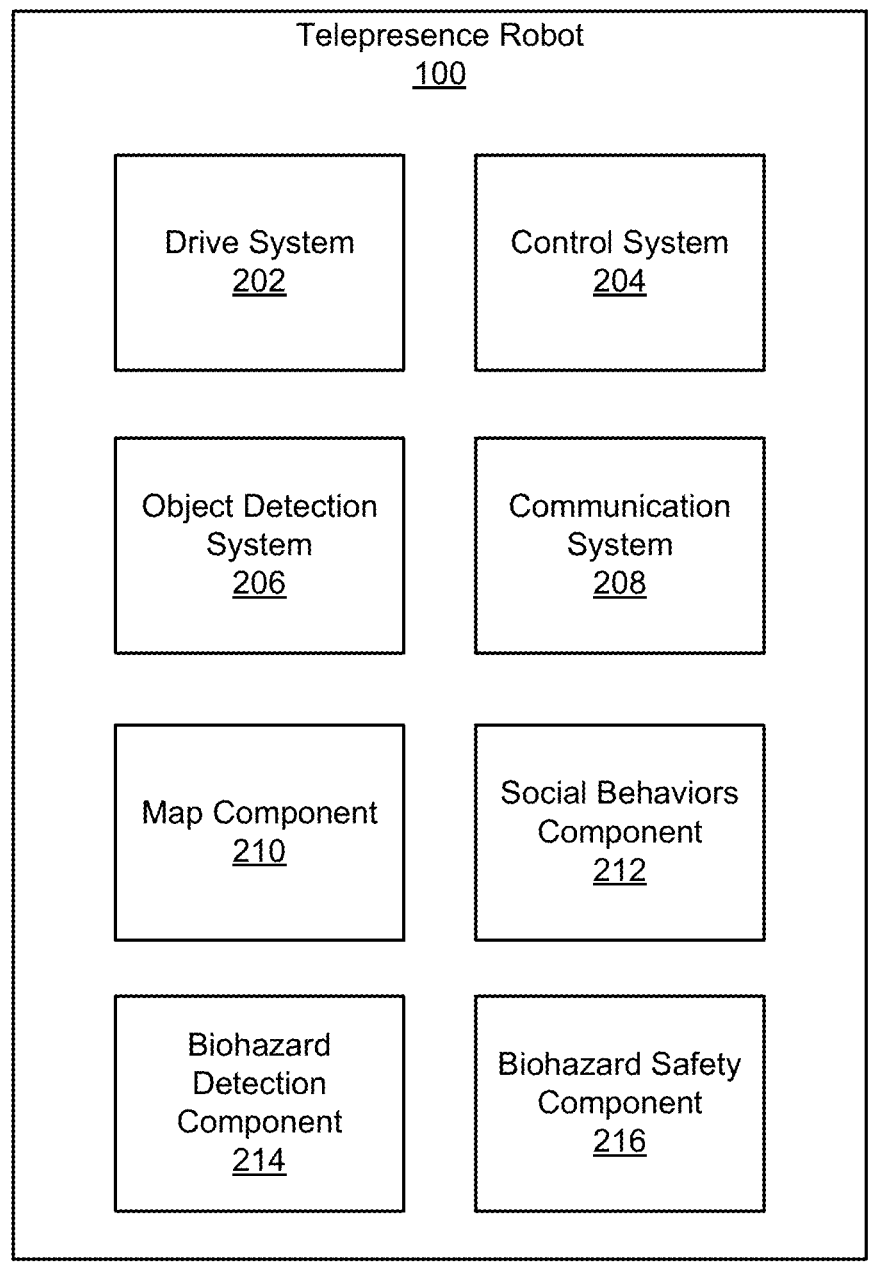
FIG. 2 is a schematic block diagram illustrating example components of the telepresence robot of FIG. 1.

FIG. 2 is a schematic block diagram illustrating example components of the robot 100 of FIG. 1. In the depicted embodiment, the robot 100 includes a drive system 202, a control system 204, an object detection system 206, a communication system 208, a map component 210, a social behaviors component 212, a biohazard detection component 214, and a biohazard safety component 216. The components 202, 204, 206, 208, 210, 212, 214, and 216 are provided by way of example only and may not be included in all embodiments. For example, various embodiments may include any one or any combination of two or more of the components 202, 204, 206, 208, 210, 212, 214, and 216, without limitation.

The drive system 202 may include one or more motors, wheels, or other hardware to move the robot 100. The drive system 202 may be configured for navigation on a variety of surfaces such as concrete, linoleum, carpet, or the like. In one embodiment, the drive system 202 is configured to provide traction and the ability to move through many of the environments found in a hospital. In one embodiment, the drive system 202 is an omnidirectional drive system that allows the robot 100 to move in any direction.

The control system 204 is configured to control the robot 100. The control system 204 may receive input from the various other components, such as components 202, 206, 208, 210, 212, 214, and 216, and generate instructions to move or otherwise control the robot based on the input. For example, the control system 204 may be configured to control the drive system 202 to navigate the robot 100 around a work area.

The control system 204 may be configured to control the robot 100 according to a variety of different operating modes. In one embodiment, the control system 204 is configured to operate the robot 100 according to an autonomous mode. In the autonomous mode, the control system 204 may control the robot 100 to navigate and perform a variety of tasks with no human input. For example, the control system 204 may cause the robot 100 to navigate through a work area and/or perform tasks without human input.

In one embodiment, the control system 204 may cause the robot to perform tasks it is capable of performing on its own and request help from a human when needed. For example, the robot 100 may be configured to open closed doors, request help with closed doors, and/or wait for a closed door to be opened. For example, automatic doors may be opened by the robot 100. The robot 100 may include a key fob or other identifying tag or information to open secure access doors. The robot 100 may be configured to monitor for people following it through secure areas and provide an appropriate alert. In some embodiments, the robot 100 may wait patiently for a door to open or actively request assistance from nearby humans. The robot 100 may have a time out period after which it may find a new path that does not require the door to be opened. Alternatively, the robot may wait patiently for a predetermined amount of time, after which it may begin requesting help. In some embodiments, the robot 100 may track statistics associated with the amount of time it waits or receives help at each door and utilize the information during route planning.

The robot 100 may be configured to proactively request human help if it is presented with a situation that it is not programmed to respond to. The robot 100 may request help via various methods, such as sending an SMS or other electronic message, using its display interface 108 to communicate its need for assistance, or utilizing other communication methods. In some embodiments, a remote operator can be summoned for manual assistance with the situation, allowing the robot 100 to reassert its autonomy.

In a semi-autonomous mode, the control system 204 may receive instructions from a user and then operate autonomously to accomplish the instructions. For example, a user may provide an instruction to navigate to a specific patient room. The control system 204 may then navigate to the patient room autonomously, accounting for objects, individuals, routes, or other information to arrive at the room in a timely and safe manner. The control system 204 may receive input from the other components 202, 206, 208, 210, 212, 214, and 216 to navigate in a social and safe manner.

In a manual mode, the control system 204 may perform instructions as provided by a user. For example, a user may remotely drive the robot 100 using a joystick or other input device or method and the control system 204 may cause the drive system 202 to move the robot 100 in the manner defined by the user. Of course, some aspects of the operation of the robot 100 may still be automated and may not require explicit instruction from a user. In any of the manual, semi-autonomous, or autonomous modes, a user may be able to remotely operate (or tele-operate) and/or view information provided by the robot 100.

According to one embodiment, changes in operation mode may be accompanied by variations in restrictions on the operation of the robot 100. For example, the robot's maximum allowed speed in a manual mode may be increased, and the remote user may be able to navigate the robot 100 into regions from which the robot 100 may be locked out in an autonomous mode. In another embodiment, the remote user may be able to override obstacle avoidance to approach people or obstacles closely, or even touch them. This may be specifically useful during teleoperated consultations, such as with a coworker, client, or patient.

With regard to humans present with the robot 100, the robot 100 may contain manual intervention functions such that a person may stop or delay the robot 100. These may be useful if the robot 100 is getting in the way of current events in the work area or to prevent accidents or other problems. In some embodiments, the display interface 108 may contain a large "stop" button, which when pressed may cause the robot 100 to halt motion and display a "resume" button. A person may thereby stop or delay the robot 100 until the person manually resume its motion, or until an internal timer sets the robot 100 back in motion. The robot 100 may also halt as a result of being manually shoved. In either case, the robot 100 may start an internal timer that will count down a pre-determined amount of time until the robot 100 resumes its course. In some embodiments, the display interface 108 may display a message that indicates how long before the robot 100 resumes motion. A person may have the option to set the robot 100 back into motion immediately by selecting a "resume" button, or to keep the robot 100 stopped by selecting a "remain stopped" button. In another embodiment, if the person selects the "remain stopped" button, the time the robot 100 is to remain halted will increase. The person may be able to select the "remain stopped" button a number of times to increase the halt time of the robot 100 up to a certain maximum time.

In other embodiments, the robot 100 may resume navigation and/or motion immediately after being shoved and/or a "stop" button is selected. In still other embodiments, the robot 100 may remain permanently stopped until further input is provided in response to a "stop" button being pushed and/or in response to a shove. The robot 100 may be configured to go into a freewheel mode when stopped, such that the robot 100 is able to be moved or shoved out of the way. In some embodiments, the robot 100 may selectively enter a freewheel mode depending on the surface it is on. For example, it may not enter a freewheel mode if it detects that it is on an inclined surface. When stopped, the robot 100 may include an "enter freewheel mode" selection on the display interface 108 that may be selected to cause the robot 100 to enter the freewheel mode. A person present with the robot 100 may thereby be able to position the robot 100 in a location out of the way of a current procedure or event.

The object detection system 206 may detect the presence of an object, human, or other physical feature that is near the robot 100. The object detection system 206 may be used by the robot 100 to detect three-dimensional information about its environment and may provide this information to the control system 204 or other component to affect navigation of the robot 100. The object detection system 206 may use a variety of sensors, cameras, or other devices to detect information about the environment of the robot 100. For example, the robot 100 may include stereo cameras, a laser range finder, a radar system, a sonar system, and/or any other system for observing and/or detecting objects or features nearby.

The object detection system 206 may use any of a wide variety of known system and methods of motion detection, facial recognition techniques, and/or other detection algorithms to detect individuals and/or objects. For example, a robot or related system may utilize binary pattern-classification techniques, Viola-Jones object detection frameworks, speeded up robust features (SURF) as local descriptors for facial recognition and detection, edge matching (e.g., Canny edge detection), greyscale matching, gradient matching, histograms of receptive field responses, scale invariant feature transforms (SIFTs), and other techniques known in the art. Such techniques may also be fused with face-detection and/or used in combination.

The object detection system 206 may be configured to discern a human from other objects using any of the above methods and may further use motion detection, face detection, feature classification for body shapes, and/or other suitable techniques. The object detection system 206 may also be used to detect a type of object. For example, using methods such as SIFT-based object detection, the robot 100 may identify objects such as beds, chairs, carts on wheels, intravenous (IV) poles, open drawers, or other common objects.

The communication system 208 may be used to provide communication to and from the robot 100 to other devices and remote users. The communication system 208 may allow the robot 100 to communicate wirelessly with a control center, remote user, on-site workers or staff, or the like. The communication system 208 may allow instructions to be sent to the robot 100 and may allow the robot to provide information regarding its current location, status, or other information. For example, the communication system 208 may provide a captured video feed to a remote client and may receive a client video feed of a user at the remote client. The client video feed may be displayed on the display screen 110 for viewing by local humans.

The map component 210 may determine a location of the robot 100 within the work area. For example, the robot 100 may have access to maps for a healthcare facility or other work area. In one embodiment, the robot 100 may maintain, create, and/or download maps of its work area. The maps may be annotated and/or marked with various features and/or describe how the robot 100 should behave in various zones or regions. The map may include various areas that are off limits as well. Some regions or areas of a healthcare facility, hospital, or other work area may be unmapped. In some embodiments, the robot 100 should avoid and/or be restricted from unmapped areas. In some embodiments, the robot 100 may avoid unmapped areas in an autonomous mode, but allow for manual tele-operation within the unmapped regions. The robot 100 may be configured to warn a user when crossing a boundary between a mapped area and an unmapped area.

In one embodiment, map component 210 may be configured to map the unmapped areas as the robot 100 autonomously navigates or is tele-operated within unmapped areas. The robot may be configured to memorize a path within an unmapped area as it is operated in a manual or semi-manual mode sufficient for the robot 100 to retrace its path back to a mapped area. The robot 100 may then localize itself at the spot the robot 100 crossed the boundary.

The map component 210 may be able to determine where within a map the robot 100 is located. In some embodiments, the robot 100 may be configured to indicate locally (e.g., lights, audible warnings, a message on a display interface) or remotely (e.g., a wireless message) that it is lost when the map component 210 is unable to determine the location of the robot 100. A user may be alerted and help guide the robot 100 to a mapped region. The robot 100 may be guided locally, such as through a follow option described herein, or be tele-operated and manually driven to a mapped region.

Examples of mapping systems, tags, and robots, and interactions there between are described in U.S. patent application Ser. No. 13/360,579 filed on Jan. 27, 2012, titled "INTERFACING WITH A MOBILE TELEPRESENCE ROBOT," which application is hereby incorporated by reference in its entirety, and in U.S. patent application Ser. No. 13/360,590 filed on Jan. 27, 2012, titled "INTERFACING WITH A MOBILE TELEPRESENCE ROBOT," which application is hereby incorporated by reference in its entirety.

The social behaviors component 212 determines operations for the robot 100 to perform to operate according to social protocols to reduce anxiety or discomfort of nearby humans. For example, if a robot moves in an erratic manner or comes too close to nearby people, those people may be uncomfortable and may find the presence of the robot to make it harder to relax, move between locations, or go about their duties. The social behaviors component 212 may determine various actions for the robot 100 that allow the robot 100 to operate around others without being a distraction or causing problems. According to one embodiment, the social behaviors component 212 will determine actions or operations to be performed based on a detected status, environment, or individual. The social behaviors component 212 may cause the robot 100 to operate differently based on the detected status, environment, or individual.

Figure 3:
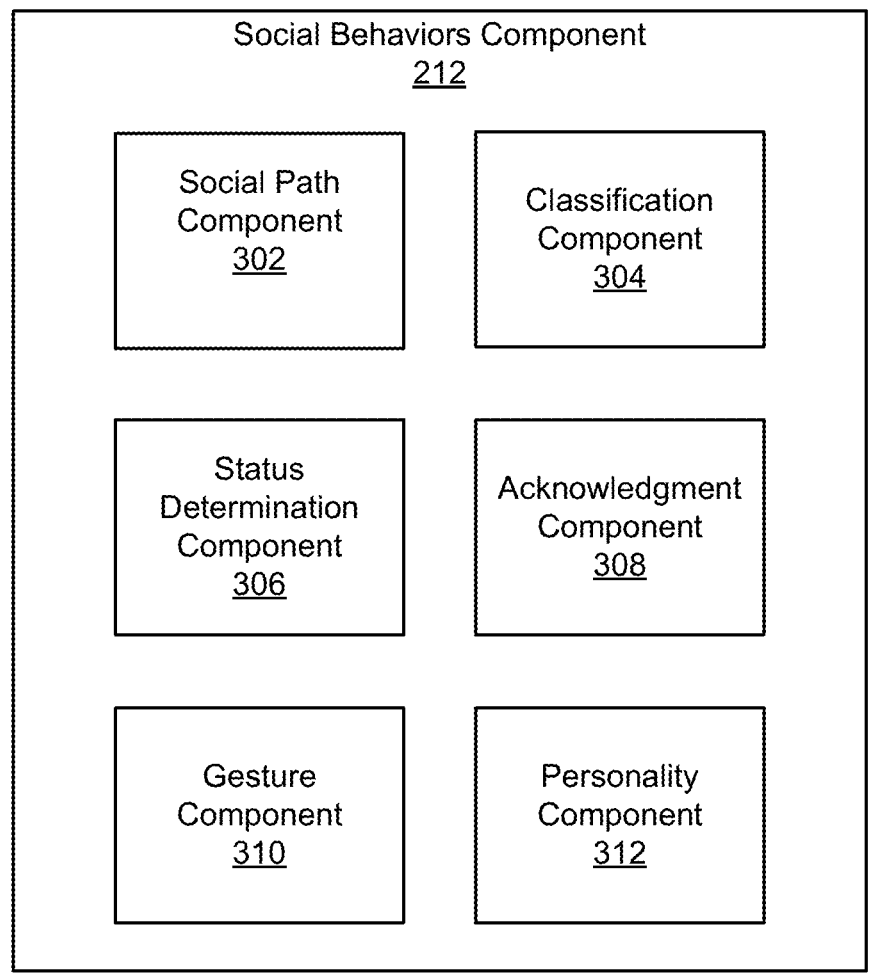
FIG. 3 is a schematic block diagram illustrating example components of a social behaviors component.

FIG. 3 is a block diagram illustrating example components of the social behaviors component 212 of FIG. 2. In the depicted embodiment, the social behaviors component 212 includes a social path component 302, a classification component 304, a status determination component 306, an acknowledgment component 308, a gesture component 310, and a personality component 312. The components 302, 304, 306, 308, 310, and 312 are provided by way of example only and may not be included in all embodiments. For example, various embodiments may include any one or any combination of two or more of the components 302, 304, 306, 308, 310, and 312 without limitation.

The social path component 302 creates or modifies paths to maintain a socially acceptable distance from humans. In one embodiment, the social path component 302 creates paths based on the current status of the robot 100 or a detected person. In one embodiment, the current status includes the presence of a person. In one embodiment, the social path component 302 creates a path according to a first set of rules when a human is not present and creates a path according to a second set of rules when a human is present. In one embodiment, the first set of rules maximizes avoidance of collision with objects and the second set of rules maximizes collision avoidance with humans. For example, the first set of rules may cause the robot 100 to navigate down the middle of a navigable area, such as a hallway. This may maximize the distance between the robot and walls or objects near the walls. On the other hand, the second set of rules may cause the robot 100 to navigate down a side of the navigable area, such as to the left or the right of the center of the hallway when a human is detected. This may meet social expectations in the location of the robot 100. For example, in some cultures it is more common to stay to the right side of a pathway or hallway whereas in others it is more common to stay to the left side. The social path component 302 may cause the robot 100 to follow these customs when a person is detected.

Similarly, the distances between objects may vary between a set of rules for use when a human is not detected and a set of rules for use when a human is detected. For example, the social path component 302 may require that the robot 100 stay further away from objects when a human is not present than when a human is present. This may allow the robot 100 to provide a greater distance between the robot 100 and the human to help avoid collision with the human but also to allow the human to feel more comfortable. Similarly, a minimum distance between a human and the robot 100 may be greater than a minimum distance between an object and the robot 100.

The social path component 302 may be configured to cause the robot 100 to operate more efficiently and quickly when humans are not present than when humans are present. For example, the social path component 302 may allow for a greater top speed of the robot 100 as it travels a path without any humans around than when the humans are around. As another example, the social path component 302 may allow for a greater acceleration rate of the robot 100 as it travels a path without any humans around than when the humans are around.

The social path component 302 may be configured to cause the robot 100 to operate more predictably to a human when humans are present. This may allow for the human to be better able to predict the robot's path and thereby avoid the human bumping into the robot 100 or the robot 100 bumping into the human. Similarly, this may reduce the chance of the robot 100 getting closer to the human than the human would find comfortable. In one embodiment, the social path component 302 may cause the robot 100 to act more predictably to a human by reducing acceleration rates of the robot. These acceleration rates may include accelerations to speed up the robot 100, slow down the robot 100, or cause the robot 100 to change direction. Slower rates of acceleration may also be achieved by creating smoother and more rounded paths for the robot 100 to follow.

Figure 4:
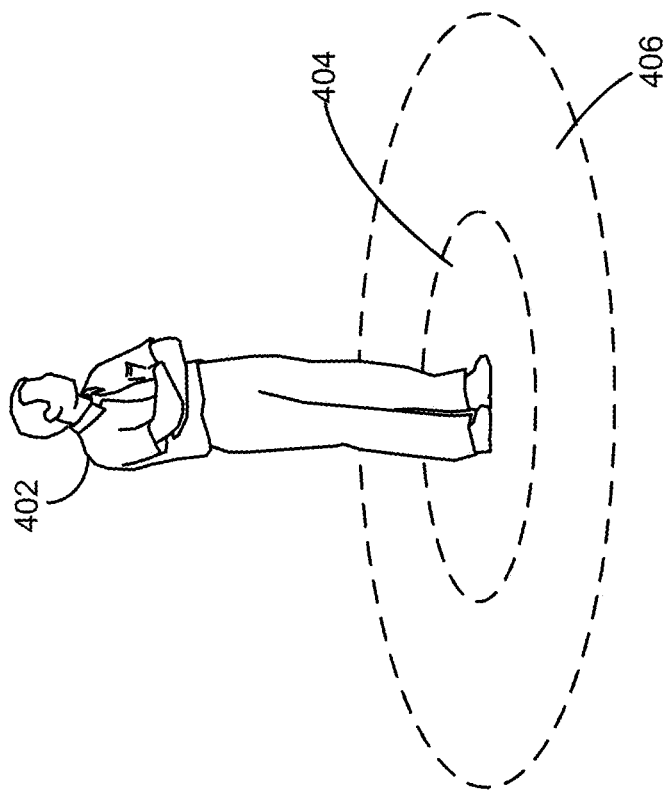
FIG. 4 is a perspective view illustrating a robot and a comfort zone and lockout zone around a human.
Figure 4:
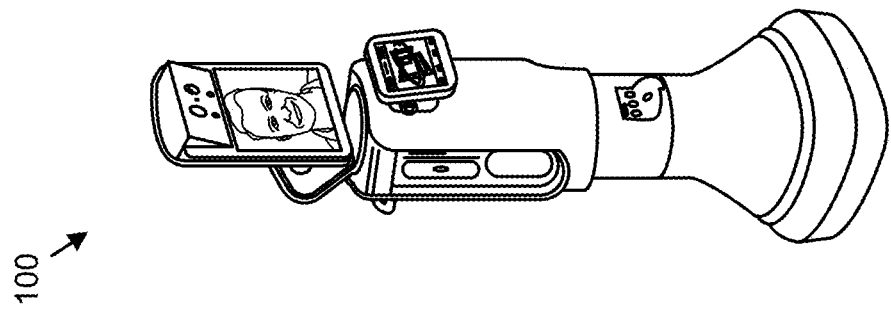

In one embodiment, the social path component 302 causes the robot 100 to reduce discomfort of nearby humans by observing a lockout zone and/or a comfort zone for each detected human. FIG. 4 illustrates a robot 100 and a nearby person 402. A lockout zone 404 and a comfort zone 406 for the human are illustrated. According to one embodiment, the social path component 302 may determine the size and shape of the lock out zone 404 and comfort zone 406. The social path component 302 may cause the robot 100 to avoid traveling through the lockout zone 404 and/or the comfort zone 406.

According to one embodiment, the lockout zone 404 defines an area through which the robot 100 may not pass. The social path component 302 may create or modify any path to avoid the lockout zone 404. The comfort zone 406 defines an area through which the robot 100 may pass, but must do so at a reduced maximum speed. In one embodiment, the social path component 302 may avoid passing through the comfort zone 406 as long as it is faster to pass around the comfort zone than slow down while passing through the comfort zone 406. By observing the lockout zone 404 and the comfort zone 406, the robot 100 may avoid making people feel uncomfortable by violating their personal space.

The lockout zone 404 and comfort zone 406 are given by way of illustration only. Similar lockout zones 404 and/or comfort zones 406 may also be used in relation to objects. The social path component's 302 path planning may allow for a relatively large lockout zone 404 or buffer space for people and a relatively small lockout zone 404 or buffer space for objects. For example, the radius of the lockout zone 404 for objects may be limited to between 0.5 and 12 inches; whereas, the radius of the lockout zone 404 for humans may be between 18 and 36 inches. This lockout zone 404 may be variable, depending on the cultural context the robot 100 is in, the amount of available space, the identity of the person, a classification of the person, a zone within a work area where the person 402 and the robot 100 are located, and/or the urgency with which the robot 100 is navigating. In some embodiments, the size of the buffer zone may be selected by a user and/or disabled by a user, such as a user who is remotely operating the robot 100. Based on the cultural context, if the robot 100 is deployed in a crowded city, it may use a 12-inch radius for a lockout zone 404 for a human. However, if the robot 100 is deployed in a less crowded city, the social path component 302 may use an 18-inch radius for a lockout zone 404.

Lockout or buffer zones may be adapted and specified for particular objects, situations, and/or locations. Merely by way of example and not limitation, the Table 1 represents possible lockout radii and comfort zones for various objects:

TABLE 1

| Detected Object | Lockout radius | Comfort zone |
|---|---|---|
| Bed | 12" | 18" |
| Chair | 8" | 12" |
| Cart on Wheels | 10" | 16" |
| Open drawer | 8" | 12" |
| Shelf, Countertop or Desk | 8" | 12" |
| Misc. medical equipment | 10" | 16" |
| Closed door | 12" | 18" |
| Gurney, stretcher | 12" | 18" |
| IV pole with bag | 10" | 16" |
| Wheelchair | 12" | 18" |

In various embodiments, the robot 100 may be configured to maintain socially acceptable distances for a wide variety of situations. Examples of managing natural social distances and other human-like behavior that may be performed by the robot 100 are described in U.S. patent application Ser. No. 11/541,422 titled "COMPANION ROBOT FOR PERSONAL INTERACTION," filed on Sep. 29, 2006, which application is hereby incorporated by reference in its entirety. For example, the robot 100 may be configured to make various gestural cues as the robot 100 moves or interacts with people.

In various embodiments, the robot 100 may act in a manner consistent with social protocols with regard to its speed. For example, the robot 100 may decelerate its traveling speed when it comes within a larger comfort zone 406 of a person 402. For example, if the lockout zone 404 has a radius of 18 inches, the larger comfort zone 406 may have a radius of 24-48 inches. The robot 100 may decelerate when it nears or enters this larger comfort zone 406. In one embodiment, the robot 100 may have a maximum speed of 5 mph with no humans around, and may decelerate to 2 mph when it enters the larger comfort zone 406. Accordingly, the robot 100 may travel at an average human walking speed within the environment of a heath care facility, taking into account the natural tendency of humans to slow down when in crowded situations or when close to other humans. For example, the robot 100 may determine an average walking speed of a detected individual and maintain the same average speed.

The classification component 304 may classify a detected person. For example, a classification component 304 of a robot 100 in a hospital may classify a detected person as one or more of a patient, a visitor, and a hospital worker. The classification component 304 may classify a person based on facial recognition, detection of a badge or wireless identification tag on the person, by location within a wheelchair or bed, by location in a work area, and/or by physical features. For example, the robot 100 may classify patients from other humans in the facility using a method such a SIFT-based identification to distinguish people located on a bed, gurney, or wheelchair.

Figure 5:
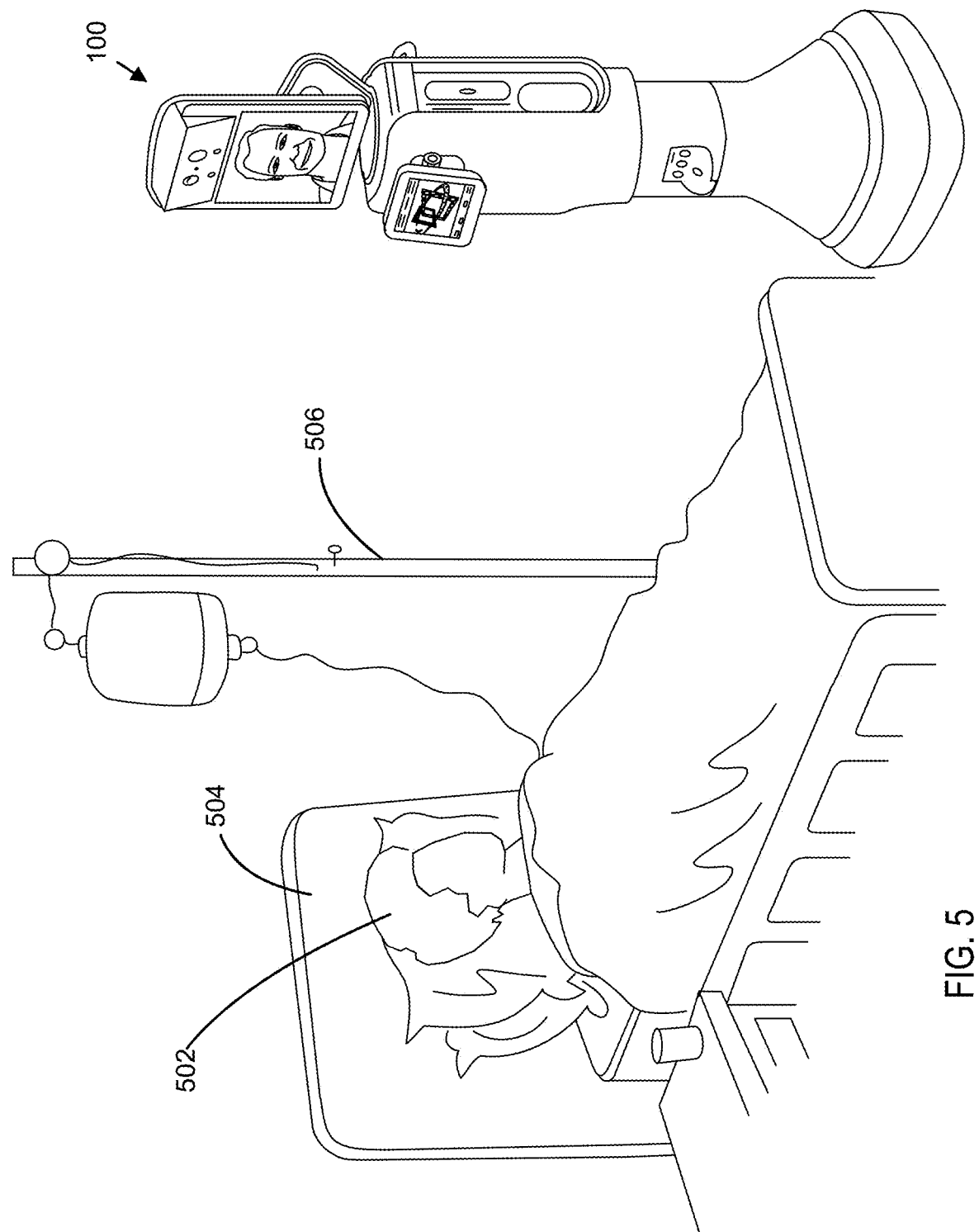
FIG. 5 is a perspective view of a robot near a patient in a bed.

FIG. 5 is a perspective view of a the robot 100 near a patient 502 in the patient's room. The patient 502 is shown within a hospital bed 504 and near an IV pole 506. In one embodiment, the classification component 304 may classify the patient 502 as a patient based on the patients location within the bed 504 and near the IV pole 506. The social path component 302 may cause the travel speed of the robot 100 to vary when it is in close proximity to a patient. In one embodiment, a patient room may act as a "patient zone," such that any person 402 in the room would be classified by the robot 100 as a patient. When the robot 100 detects a patient, it may increase the lockout zone 404 and comfort zone 406 radii from that of other people 402 in the hospital and/or adjust the speed limits for a given type of zone. In one embodiment, this ratio may be 1:1.5. Thus, for example, the lockout zone 404 radius may increase from 12 inches to 18 inches, and the comfort zone 406 radius may increase from 18 inches to 27 inches. This may serve to protect patient safety and/or patient emotional security, especially because patients may be in a sensitive emotional or physical state.

The social path component 302 may create a navigation path based on a classification of a nearby person. For example, when the robot 100 is near a patient or visitor in a hospital work area, the social path component 302 may afford greater distances to ensure that the visitor or patient is not disturbed. The social path component 302 may allow for a smaller lockout zone 404 or comfort zone 406 for hospital employees, such as doctors or nurses, than for visitors and patients.

The status determination component 306 determines a current status of the robot 100 or of a nearby person 402. For example, the status determination component 306 may determine whether there is an emergency, whether there is a human present, whether humans are engaged in a conversation, whether the robot 100 will navigate near an intersection, whether the robot 100 will navigate near a doorway, or other possible statuses of the robot 100 or a nearby person 402.

The status determination component 306 may determine that the current status includes nearby people involved in a conversation. The status determination component 306 may determine that two or more people are involved in a conversation and avoid passing between them. For example, the status determination component 306 may determine a conversation zone that includes a continuous region between the human and the one or more humans such that the telepresence robot cannot pass between the human and the one or more humans without passing through the conversation zone.

Figure 6:
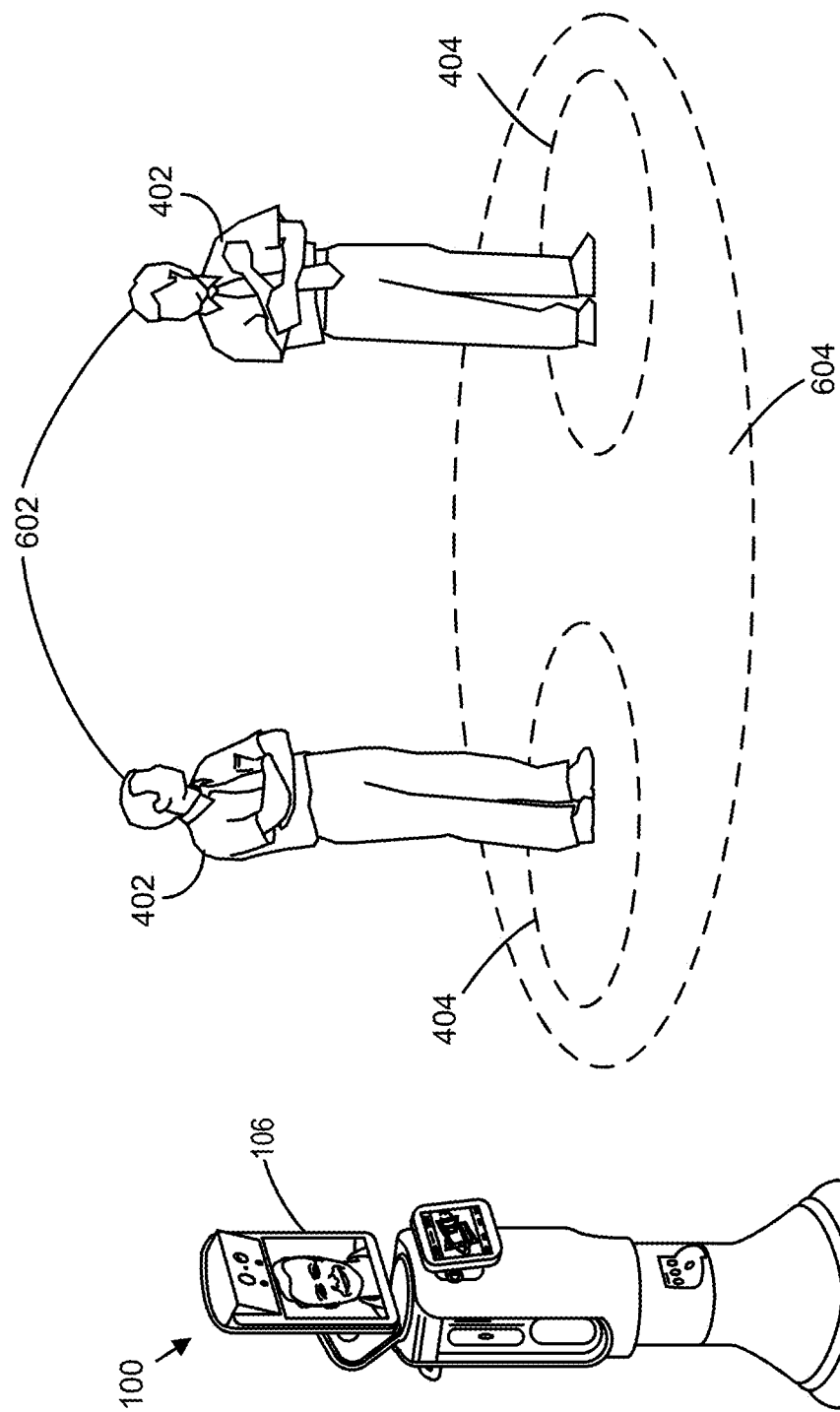
FIG. 6 is a perspective view illustrating a robot and a conversation zone and lockout zones around a group of humans.

FIG. 6 illustrates a robot 100 near two people 402 who are engaged in a conversation. The robot may recognize the people 402 as part of a conversational group 602 and avoid disturbing them by not moving in between the people 402. The robot 100 may be configured to plan its navigational path around clusters of humans, so as to avoid interrupting human interaction. The robot 100 may scan a room to detect humans clustered in groups 602 that may potentially be in conversation. In one embodiment, the robot 100 may scan a room to detect humans and then perform a segmentation and clustering analysis to detect potential conversational groups 602. From this analysis, the robot 100 may determine which direction the humans are facing, their proximity to other humans, hand gestures, or other actions indicating a group 602 of interacting humans. In other embodiments, the robot 100 may utilize sound detection techniques and/or analysis to identify humans that are potentially in a group 602. FIG. 6 illustrates a conversation zone 604 and respective lockout zones 404 for each person 402. The social path component 302 may avoid the conversation zone 604 similar to how it avoids a comfort zone 406. Alternatively, when human groups 602 are detected, the robot 100 may apply a lockout zone 404 and/or comfort zone 406 to the entire group 602, as opposed to individual humans within the group 602. Accordingly, the robot 100 may avoid interrupting conversations between humans in a group 602 and may treat the conversation zone 604 similar to a lockout zone.

Similarly, the status determination component 306 may determine other groups of people and/or objects that the robot 100 should not pass between. In addition to attempting to abide by social protocols when navigating around humans, the robot 100 may also adhere to specific behavioral protocols when navigating around specific objects common to healthcare facilities. In some embodiments, the robot 100 may have special, pre-determined lockout radii and/or comfort zones for each respective object. Other objects may trigger special-case behaviors. For example, when the robot 100 finds a cable or cord, it may determine whether to traverse or avoid the cable depending on the cable's height. In other embodiments, the robot 100 may alter its behavior based on alerts or existing conditions. For example, the robot 100 may alter its behavior based on a "floor cleaning" sign. In such an example, the robot 100 may respond by slowing its speed to 50% and staying within a few inches of a wall. Another example may include the robot 100 detecting a patient with an IV pole or walker, which may cause the robot 100 to avoid navigating between the patient and the IV pole or walker.

Figure 7:
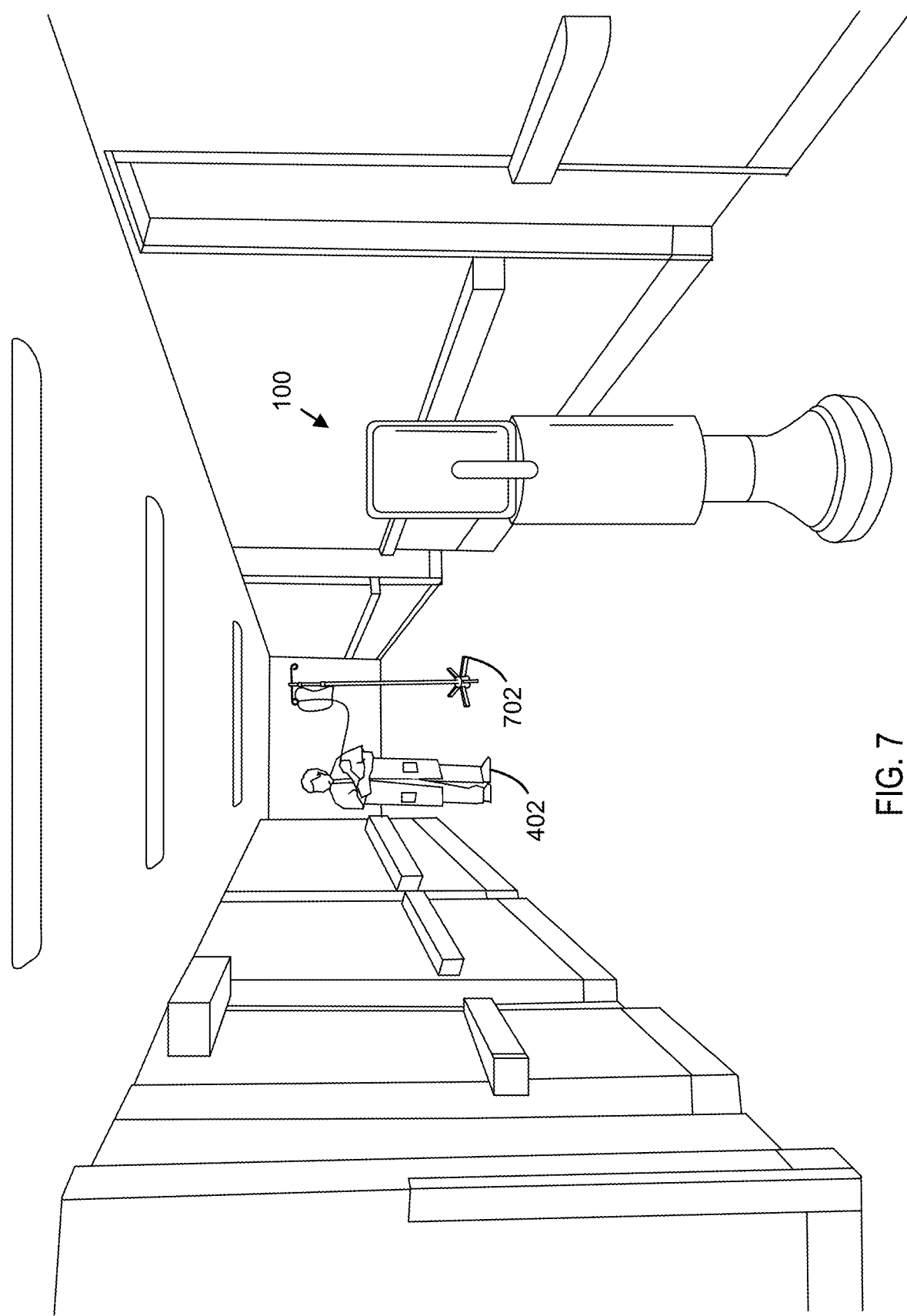
FIG. 7 is a perspective view of a robot approaching a patient and intravenous pole in a hallway.

FIG. 7 illustrates a perspective view of the robot 100 approaching a person 402 and an IV pole 702 in a hallway. According to one embodiment, the object detection system 206 detects the person 402 and IV pole 702 and the status determination component 306 determines that the robot 100 should not pass between a person 402 and an IV pole 702 based on a stored rule. For example, even though the robot 100 may not be able to see tubing running between the person 402 and the IV pole 702 the robot may follow a rule that the robot 100 should not pass between them. Thus, the social path component 302 may plan a path around the person 402 and IV pole 702 that does not involve passing between them.

The status determination component 306 may determine that the current status includes that the robot 100 is approaching a doorway or intersection. The status determination component 306 may determine that the robot 100 is approaching a doorway or intersection based on information detected by the object detection system 206 and/or based on a current location of the robot 100 as determined by the map component 210. The status determination component 306 may notify the social path component 302 of the upcoming doorway or intersection and the social path component 302 may determine a path to pass through the doorway or intersection while limiting chances of entering a lockout zone 404 of any people 402 or bumping into any objects or people. For example, the social path component 302 may determine an entry angle through the intersection or doorway to increase visibility to any approaching humans. Similarly, as the robot 100 approaches the doorway or intersection, the status determination component 306 and/or the social path component 302 may determine whether a human will reach the intersection within a threshold time of the robot 100. If the human and the robot 100 will likely cross around the same time the social path component 302 may modify a path of the robot 100 to avoid a lockout zone 404 for the human. The social path component 302 may change the path such that the robot 100 stops at the intersection, speeds up, slows down, or even moves sideways to avoid coming within a lockout zone 404 and/or comfort zone 406 of the human.

The social path component 302 may also avoid sudden, unexpected changes in direction or movements that might potentially surprise or disturb a human.

Figure 8:
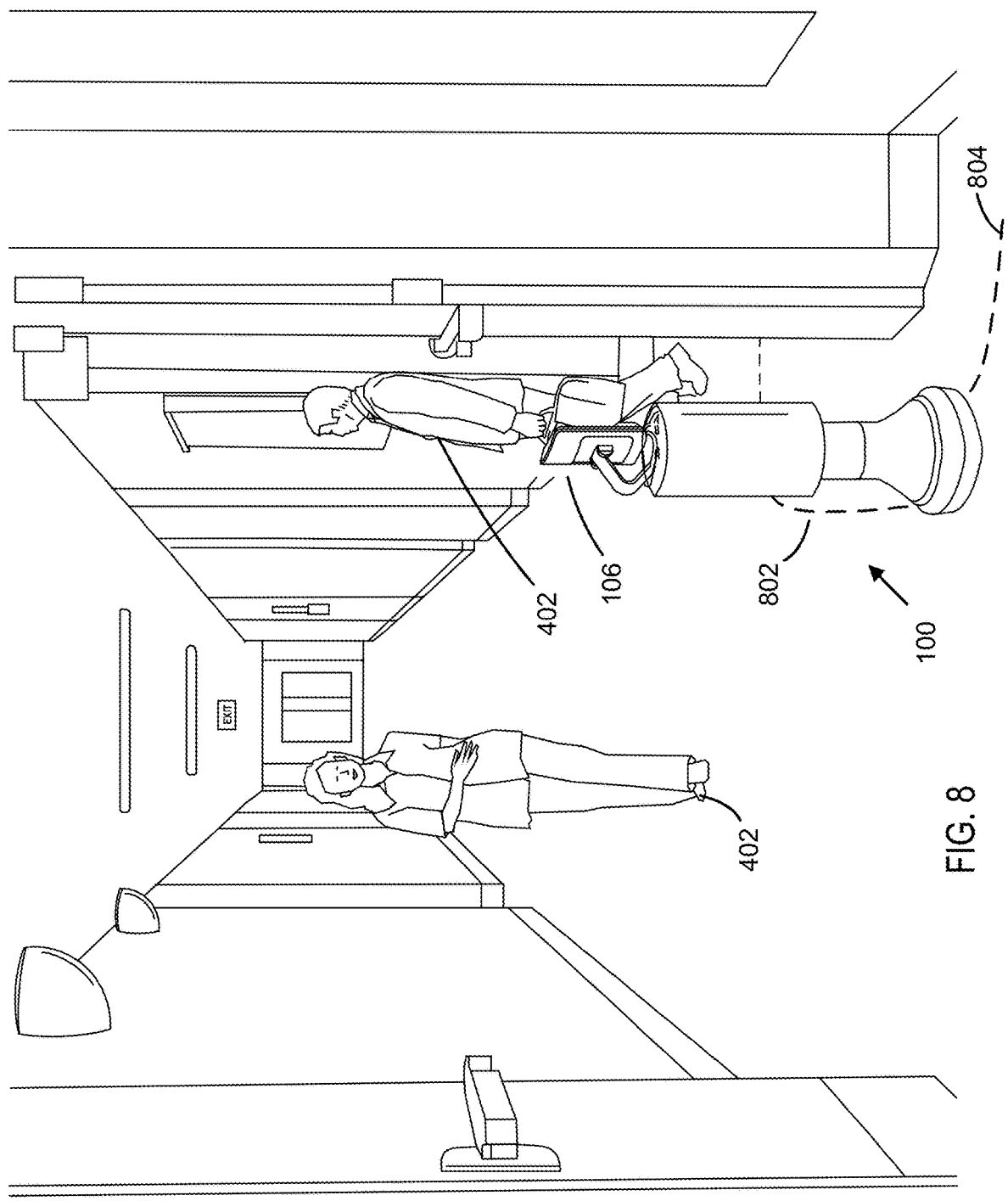
FIG. 8 is a perspective view of a robot approaching an intersection.

FIG. 8 illustrates a perspective view of a robot 100 as the robot 100 navigates around a corner at an intersection. The robot 100 is shown approaching the intersection while two people 402 are also passing through the intersection. A planned pathway 802 is shown around the corner of the intersection that will be predictable for the people 402. For example, the pathway 802 is a smooth rounded pathway and sweeps wide around the corner to increase visibility for the robot 100 and any more people that may be coming. The social path component 302 may determine that the robot 100 will be the first to get around the corner and may thus proceed. In one embodiment, the robot 100 may determine that the people 402 will be in the intersection about the same time as the robot 100 and the social path component 302 may determine that it would be best for the robot to stop until the people 402 are through the intersection. In one embodiment, the robot 100 may determine that it has a right of way since it is turning to the right and may proceed around the corner even if the people 402 might need to wait.

With respect to thresholds in doorways or intersections, the status determination component 306 may be configured to cause the robot 100 to slow down, approach thresholds at an angle, and/or approach the threshold squarely. In some embodiments, the robot 100 may have an omnidirectional drive system 202 configured to move in any direction, regardless of the orientation or angle of the base 102 relative to the motion. However, in some embodiments an omnidirectional base may be configured to climb or traverse a raised threshold or other object better at one angle than another. Accordingly, the status determination component 306 may be configured to orient its base 102 at the optimal angle relative to a threshold prior to traversing the threshold. For example, a three- or four-wheel base 102 may traverse a raised threshold better if it is oriented squarely with respect to the threshold, such that two wheels of the base 102 contact the raised threshold at the same time. In some embodiments, thresholds may be included in a map of the healthcare facility. For example, raised thresholds for doorways may be tagged or otherwise marked on a map used by the robot 100 for navigation. In some embodiments, the thresholds may be detected by the robot 100 as it approaches them.

The status determination component 306 may determine that the current status includes that the robot 100 is being delayed during navigation. The status determination component 306 may determine that the robot 100 is being delayed during navigation when a pathway is blocked by one or more individuals and objects for at least a delay time period. The robot 100 may encounter obstacles that prevent it from passing, such as a person 402, a group 602 of people, an object, or a combination thereof. The robot 100 may attempt to plan a navigational path to avoid breaching social rules for a specified timeout period, after which it may attempt to find a new route to its destination and/or violate the social rules. In some embodiments, the timeout period may be short, such as between 1 and 30 seconds, to avoid the robot 100 hovering or dodging around people in the hallway for a long period of time while they are talking or otherwise engaged in the hallways. In still other embodiments, the robot may ask people to step aside or move.

Returning to FIG. 7, the social path component 302 may determine that it cannot maneuver down the hallway without entering a lockout zone 404 of the person 402 or IV pole 702. Upon determining the path is blocked the status determination component 306 may start a timer and continue looking for a way around the person 402 and IV pole 702. If the timer reaches a delay time the status determination component 306 may determine that the robot 100 is in a delayed navigation status. The social path component 302 may, in response, shrink a lockout zone 404 of the person 402 or IV pole 702 and then attempt to find a route through. If a path is found the social path component 302 may cause the robot 100 to continue on its path. Otherwise, the social path component 302 may seek for a new pathway.

Similarly, when located in narrow, crowded, or otherwise tight spaces, the robot 100 may leave a small buffer of space between itself and an object, but may pass relatively close to objects in order to navigate.

The status determination component 306 may determine that the current status includes that a nearby human is involved in an emergency. The status determination component 306 may determine that a nearby human is involved in an emergency based on how fast a nearby human is moving. For example, if the object detection system 206 detects that a human is moving at a fast pace down a hallway, the status determination component 306 may determine that the user is involved in an emergency or has an urgent task to perform. Similarly, the status determination component 306 may determine that a nearby person is involved in an emergency based on one or more of a speed of a moving object, a speed of a moving person, a warning sound, and flashing lights. In another embodiment, the robot 100 may detect the velocity of the approaching person or object and, if it is above a pre-determined threshold, determine that there is an emergency or dangerous situation. In this case, the robot 100 may move to the side of the hallway and wait until the passing person, group, and/or object has passed.

In one embodiment, upon determination that a person is involved in an emergency, the social path component 302 may determine a path to cause the robot 100 to move out of a high-traffic area, move out of the way of the person or object involved in an emergency, or the like. Returning to FIG. 8, the robot 100 is shown approaching an intersection. According to one embodiment, if one or both of the people 402 were moving at a faster rate than is normal for people in the work area, the robot 100 may stop and follow the other path 804, instead of the planned path 802, to get out of the way for a short amount of time or until the intersection or hallway has cleared. Similarly, the social path component 302 may determine that another location is more ideal for getting out of the way and may cause the robot 100 to navigate to the other location.

The robot may be configured to detect or receive an indication of the urgency of the approaching object. For example, the speed of an approaching gurney may be indicative of the urgency of the situation. In another embodiment, a gurney may have a transmitter or lights that indicate the urgency of the situation. The robot 100 may respond by moving out of the way. The robot 100 may also be prohibited from loitering in high-traffic areas. For example, hallways may be marked as areas where the robot 100 should not stop, or in which the robot 100 should move to one side of the hallway if it does stop.

The robot 100 may be more sensitive to emergencies in an emergency department (ED) region. For example, the robot 100 may be more likely to stop and wait at the side when people move by. For example, the robot 100 may utilize the motion and velocity detection behaviors described above, but adjust them for the ED region, such that a velocity of 50% of the normal emergency velocity threshold may be enough to trigger an emergency response behavior of waiting by a wall for the fast-moving person or object to pass. Similarly, the robot 100 may increase its lockout zones 404 and/or comfort zones 406 for objects in an ED unit to decrease the likelihood that it will collide with a shelf or table containing delicate instruments.

The status determination component 306 may determine that the current status includes that the robot 100 is involved in an emergency or has an urgent status. For example, while being remotely operated by a doctor, the doctor may select an option for urgent operation of the robot 100. In one embodiment, in response to receiving an indication that the robot 100 is involved in an emergency situation, the robot 100 may be configured to violate one or more of the social protocols discussed herein. For example, the robot 100 may violate the group conversation rule to reach a high-priority destination by traveling between two humans having a conversation. In another embodiment, the robot 100 may need to reduce the size of a lockout zone by a predetermined fraction, such as one half. Similarly, increased speed or other changes in restrictions may be followed. In addition, the robot 100 may be configured to play a sound clip of a polite phrase, such as, "excuse me" or "I'm sorry."

The status determination component 306 may determine the current status as being located within a specific region of a work area. In one embodiment, the robot 100 may have the ability to change its navigational settings depending on the different areas of the hospital through which it is traveling. In some embodiments, the map component 210 may allow the robot 100 to determine which region of the hospital it is in, and the robot 100 may adapt its operation accordingly. For example, the robot 100 may adjust behaviors, such as how far it navigates into a room, the speeds it travels, the radii of the lockout zone 404 and/or buffers between itself and objects, and other behaviors. In some embodiments, the robot 100 in an intensive care unit (ICU) region or a pediatric ward may adjust its maximum speed to 50% of its normal pace. In another embodiment, the robot 100 may navigate only a specified distance into an ICU room from the doorway. For example, the robot 100 may move only far enough into a room to view information from monitors. In this example, the rest of the room may be considered a lockout zone 404.

The social path component 302 may also allow the robot 100 to exhibit team based behavior. In one embodiment, for example, the display interface 108 on the upper portion 104 of the robot 100 may present a "follow team" option that may be selected by a user. When the follow team option is selected, the robot 100 may identify various features of a person to be followed, such as height, facial features, size, or other physical characteristics. The social path component 302 may then follow the identified individual at a predetermined distance. The robot 100 may accomplish this using the object detection system 206 that performs methods such as facial detection and/or other detection and following techniques. When following an individual, the robot's 100 speed and lockout zones may be adjusted to comply with a team-based environment. In some embodiments, the robot's 100 lockout zone may be reduced to allow it closer physical proximity to the team or followed individual, and/or the comfort zone may be reduced or eliminated entirely. In other embodiments, the speed of the robot 100 may be adjusted to match a time-averaged speed of the team or individual.

The social path component 302 may also exhibit team behavior by getting out of the way of an oncoming person. For example, the social path component 302 may cause the robot 100 to move in a human-like way in response to objects or people moving in its direction, even if they have not crossed into its navigational path. In one embodiment, the robot 100 may respond to a human presence in a hallway by moving closer to one side of the hallway, decelerating as the person or object approaches, moving to the side of the hallway and stopping until the person or object has passed, and/or by performing other human-like reactions. In one embodiment, if the robot determines that a hallway is narrow, the robot 100 may decelerate as a person and/or object approach. The robot 100 may stop next to the wall as a person and/or object approach in a narrow hallway, and resume once they have passed. In one embodiment, the robot 100 may use any of the various detection methods described above, such as a motion detection method, to choose the side of the hallway opposite of the detected movement (or choose either side of the hallway if the motion is from the center of the hallway, or the side of the hallway that is less congested with other obstacles). In one embodiment, the robot 100 may be configured to always go toward either the right or the left, based on a user specification. In another embodiment, the robot 100 may detect if the hallway is narrow and decelerate accordingly.

Figure 9A:
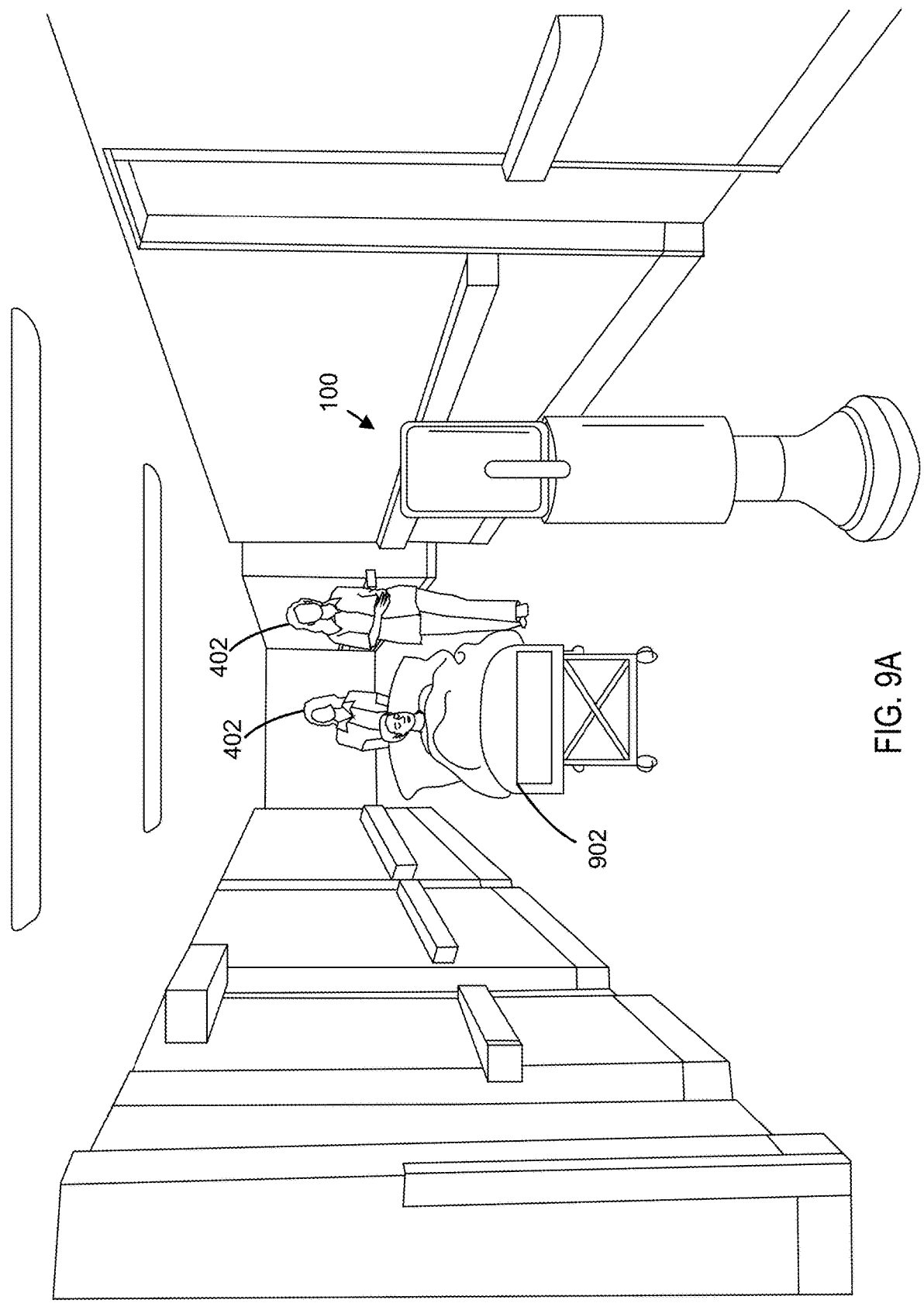
FIG. 9A is a perspective view of a robot approaching large group in a hallway.

FIGS. 9A and 9B are perspective views of the robot 100 in a hallway with some people 402 and a patient in a bed 902 approaching. According to one embodiment, the robot 100 recognizes in FIG. 9A that the people 402 and the patient in the bed 902 take up most of the hallway and are moving toward the robot 100. The social path component 302 may determine that the robot 100 should move over and let the people 402 and the patient in the bed 902 pass. In FIG. 9B, the robot 100 has followed a path 904 to a side of the hallway and stopped to let the people 402 and the patient in the bed 902 pass. The robot 100 may then proceed on its way once the group has passed.

The acknowledgment component 308 may be configured to provide acknowledgement or other visible information to nearby humans. For example, the acknowledgment component 308 may be configured to cause the robot 100 to socially acknowledge a human, indicate a direction to be traveled by the robot, indicate a state or status of the robot 100, apologize for violating a social rule, or the like. The acknowledgment component 308 may provide the acknowledgement or indications visually, audibly, or using a gesture.

The acknowledgment component 308 may provide acknowledgment or other indications using the lights 114. For example, the acknowledgment component 308 may us the lights 114 or other lights located on the base 102, upper portion 104, head, front, back, and/or other areas to indicate direction, intended direction, urgency, or usage, and/or to set a mood. In one embodiment, if a pathway is blocked by a human the acknowledgment component 308 may flash the lights 114 to get the attention of a person blocking the path. Various colors of lights 114 may be associated with moods and/or contexts. For example, blue may be calming or soothing, while red or yellow may indicate an emergency. The lights may also indicate if a robot 100 is being tele-operated or is autonomously navigating.

In one embodiment, the acknowledgment component 308 flashes the lights 114 to indicate that the robot 100 is in an emergency or urgent status. Similarly, flashing lights may indicate that the robot 100 is delayed. For example, in the scenarios discussed above, the acknowledgment component 308 may turn on the lights 114, flash the lights 114, or the like to indicate that the robot 100 may act in a more urgent manner and may pass closer and/or move more quickly than normal. For example, the robot 100 may use the lights 114 as a blinker to indicate that the robot 100 will turn to the right. Nearby people will notice the flashing lights 114 and pay attention or move out of the way of the robot 100.

The acknowledgment component 308 may provide acknowledgment or other indications by making an audible sound, such as by using a speaker. For example, the acknowledgment component 308 may also provide an audible warning, or apology, to nearby humans when it violates a comfort zone, reduced lockout zone, conversation zone, or the like. For example, the robot 100 may play an audio clip that says "I'm sorry," "excuse me," or the like. As another example, the robot 100 may play a subdued siren sound, beeping sound, or other warning sound when the robot 100 is in an urgent mode or when it has been delayed. This may provide a notification to nearby individuals that the robot 100 is there and may be trying to get by. In one embodiment, the acknowledgment component 308 causes the robot 100 to provide a social acknowledgment to a passing human. For example, the robot 100 may say "hello" or provide any other audible greeting to a passing human.

When the robot 100 needs to violate any rules, it may apologize to the humans by playing the sound clip as it passes. The robot 100 may also issue a warning before it violates a social rule. For example, a warning may be issued by playing a sound clip of a pre-recorded polite phrase. In other embodiments, this warning may be issued by flashing lights 114 on the upper portion 104 of the robot 100.

The acknowledgement component 308 may also cause a gesture component 310 to perform a gesture to indicate a status or acknowledge a passing human. For example, gestures may be performed to indicate a direction to be traveled, acknowledge the human, or the like.

The gesture component 310 may be configured to perform a gesture to indicate a direction to be traveled. For example, the gesture component 310 may cause the head 106 of the robot 100 to turn in the direction the robot 100 intends to travel. The head 106 may be turned prior to the robot 100 actually moving in that direction. This is similar to how humans often turn their head in the direction they intend to walk before moving in that direction. Humans can generally read this body language and know where a person intends to walk and can thus avoid walking in the same direction, slowing to let that person pass, or the like. Similarly, by turning its head 106 in the direction it intends to travel the robot 100 may naturally communicate a direction to be traveled to nearby humans where the robot 100 will go. This may reduce the likelihood of the robot 100 coming within a lockout zone 404 or comfort zone 406 of the person 402. This is partly because the movement is rendered more predictable to the human because of the gesture.

Similar gestures may also be performed at doorways or near other blind spots. The robot 100 may utilize a navigational algorithm that causes the robot 100 to face the direction of its motion. For instance, rather than facing forward and panning to the left or right, the robot 100 may turn its body portion and/or head portion in the direction of the movement. The robot 100 may also imitate human behavior by rotating its head portion to the left and right (scan) over a room or corridor before entering. If the head portion of the robot 100 faces a different direction than the actual movement, humans in the surrounding region may find it unnatural, disturbing, distracting, and/or otherwise be made to feel uncomfortable. Accordingly, the robot 100 may imitate human behavior by maintaining its head portion facing the direction of movement, other than for brief periods as described herein (e.g., when greeting).

In one embodiment, the robot 100 may decelerate its approach to a threshold, stop to scan the room or intersection, and then adjust its navigational path if necessary. In other embodiments, the robot 100 may not come to a complete stop, but may decelerate to a very slow speed such as between 0.1 mph and 2 mph as it scans the room or intersection.

FIG. 8 illustrates an example of a head turn gesture to indicate a direction. The robot 100 is shown turning its head 106 to the right even though the robot 100 has yet to begin moving to the right, as indicated by the path 802. In addition to gesturing, the robot 100 may provide other indications to allow hospital staff and visitors to know where the robot 100 is headed. These indicators may include the robot's head 106 facing the direction of its motion (as discussed above), or having the robot 100 turn its head 106 to "look" to the side it intends to turn when it approaches an intersection. Other indicators may include lights 114, such as light emitting diodes (LEDs), on the robot 100 that act as turn indicators. The lights 114 may be visible from the front or rear. The indicators on the appropriate side may turn on or flash a pre-determined distance from the robot's 100 turn.

The gesture component 310 may be configured to perform a gesture to acknowledge a passing person 402. The robot 100 may use a method, such as motion detection, facial recognition techniques, or other detection methods to detect humans. In one embodiment, the robot 100 may turn its head 106 to face the human briefly, and then return to face the direction of its travel. In other embodiments, the robot 100 may keep its face pointed toward the human's face for a moment, so as to simulate the equivalent of human eye contact. In other embodiments, the robot 100 may be configured to simulate a nod to the human, such as by tilting its head 106 downward, then returning its head 106 to face its forward direction. The robot 100 may also be configured to greet humans in the hallway by playing a pre-recorded sound clip of a greeting such as, "hello" or "good morning."

FIG. 9B also illustrates the head turn gesture to acknowledge the people 402. The robot 100 has moved to the side of the hallway and turned its head 106 to "look" at the passing group. The robot 100 may pan the head 106 to face the group for a short period of time to simulate eye contact. In one embodiment, the robot 100 may only pan the head 106 toward the people 402 for only a short time so that the people 402 do not feel like they are being stared down. The robot 100 may also nod the head 106 by tilting the head 106 forward and then back up. The robot 100 may also play an audible greeting.

Figure 9C:
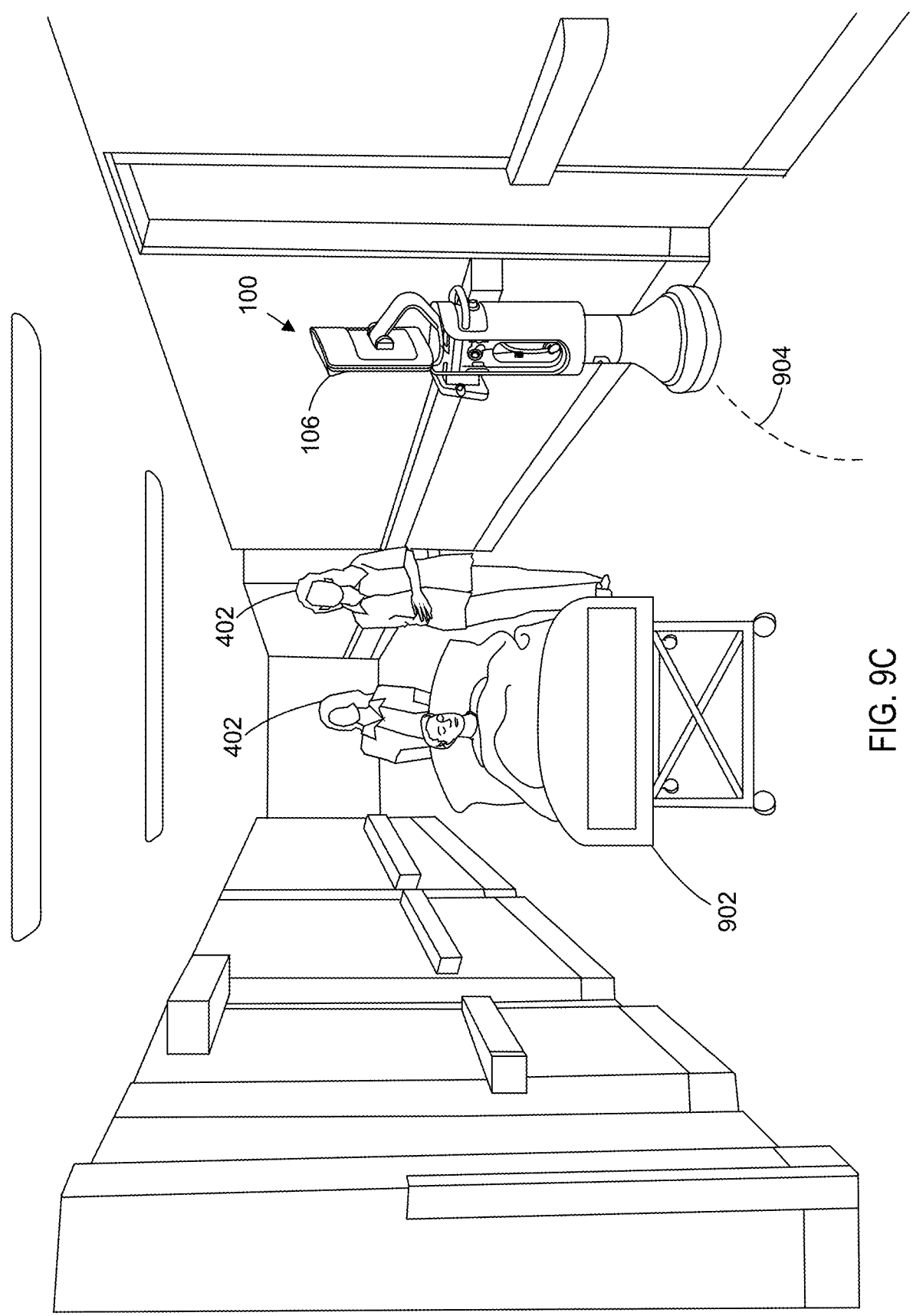
FIG. 9C is a perspective view of a robot allowing the large group of FIG. 9A to pass with a body portion rotated

FIG. 9C illustrates an alternative embodiment in which the body of the robot 100 (along with the head 106) has rotated to "look" at the passing group. Again, the robot 100 may also nod the head 106 by tilting the head 106 forward and then back up. The robot may be configured to turn only the head 106, as illustrated in FIG. 9B, or it may be configured to rotate the body as well, as illustrated in FIG. 9C.

Throughout this disclosure, the concept of a robot "turning its head" may include a robot turning a head portion relative to a body portion. Alternatively, "turning its head" may include a robot with a fixed head, and thus require that the robot rotate more than just a head portion (e.g., the upper portion 104, a base 102, or even the complete robot) in order to "turn its head" and "look" in a particular direction or at a particular object.

The personality component 312 may control the robot 100 to operate according to an assigned personality. For example, a personality may be assigned to the robot to cause it to behave in certain ways. For example, a shy robot may only nod, while an outgoing robot may greet each human verbally as it passes. Similarly, the types of acknowledgments may vary between different personality types. The personality component 312 may also cause the lights 114 to light up according to the personality type and may display a caricature corresponding to the personality type. For example, caricatures that may amuse children may be used in a children's section of a hospital.

Returning to FIG. 2, the biohazard detection component 214 is configured to detect a potential biohazard. The biohazard detection component 214 may detect the presence of a potential biohazard and/or identify a type of biohazard. For example, the biohazard detection system may include one or more sensors that detect the presence of a potential biohazard. In one embodiment, the biohazard detection component 214 includes a sensor that grazes a floor of a work area as the robot 100 moves through a work area. In one embodiment, the senor may include a moisture sensor. For example, the moisture sensor may detect spilled chemicals, blood, urine, or other fluids that may be potential biohazards. In one embodiment, the sensor may include a chemical sensor that detects the presence of one or more chemicals. For example, some chemicals may be present in different biohazard materials. The chemical sensor may allow the biohazard detection component 214 to detect the chemical and determine that a biohazard or potential biohazard is present.

In one embodiment, the biohazard detection component 214 may detect a potential biohazard by detecting material on a floor of a work area that is not part of the floor based on an image captured by a camera of the robot 100. For example, the biohazard detection component 214 may perform image analysis to detect liquid, powders, or other materials on a floor of the work area. The biohazard detection component 214 may be capable of identifying a material based on color, location, size, shape, texture, etc. Similarly, a moisture sensor or chemical sensor may also be used to identify a type of biohazard or potential biohazard.

The biohazard safety component 216 is configured to provide instructions to the control system to cause the robot 100 to prevent spreading of a detected potential biohazard. The biohazard safety component 216 may prevent spreading of the potential biohazard by stopping on or near the potential biohazard to block others from walking through the potential biohazard and spreading it throughout a work area. The biohazard safety component 216 may provide a warning to nearby humans about the detected potential biohazard. In one embodiment, the biohazard safety component 216 may cause the robot 100 to flash a biohazard symbol on the display interface 108. In one embodiment, the biohazard safety component 216 may cause the robot 100 to flash one or more lights 114 to indicate an emergency or urgent situation. In one embodiment, an audible warning may be played by the robot 100 that indicates that there is a potential biohazard and instructing humans to avoid it. In one embodiment, a biohazard symbol, flashing lights, and an audible warning may all be provided.

The biohazard safety component 216 may prevent spreading of the potential biohazard by transmitting a message that there is a detected potential biohazard. For example, the biohazard safety component 216 may cause the communication system 208 to send a message over a wireless network to indicate the location, type of potential biohazard, and/or other information about the potential biohazard. A cleaning crew or other management crew may receive the message and be able to address the problem and/or clean up the biohazard.

The biohazard safety component 216 may prevent spreading of the potential biohazard by cleaning up the biohazard. The biohazard safety component 216 may be equipped with cleaning tools to clean up a liquid, powder, or any other material. The biohazard safety component 216 may include a sterilization pad and/or drying pad to sterilize and/or dry the area where the potential biohazard was detected. Thus, the robot 100 may be capable of maintaining sanitation in a work area, such as a hospital. The robot 100 may send a message that the potential biohazard was cleaned and one or more workers may be able to double check whether there is any more cleaning that needs to be done.

Figure 10:
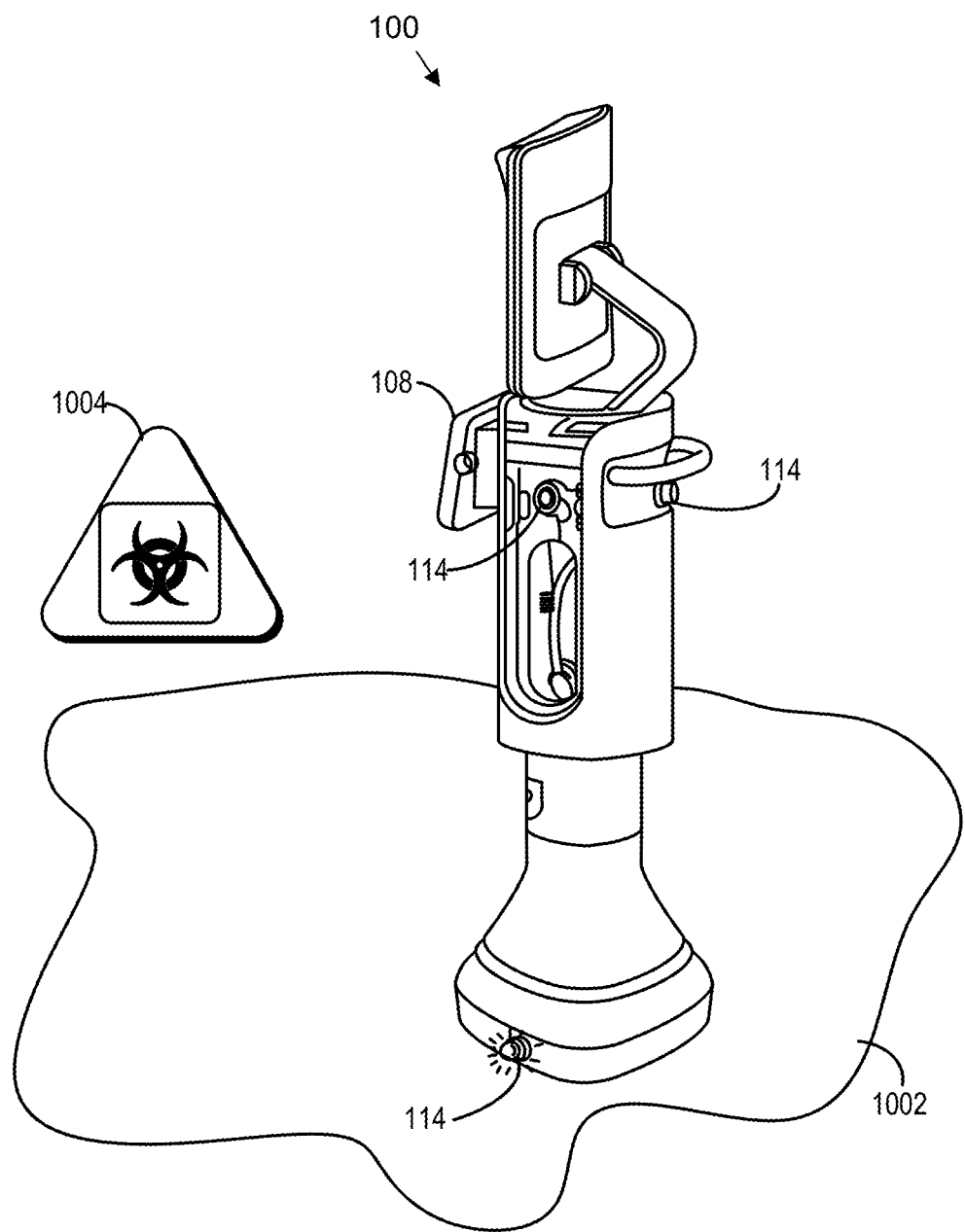
FIG. 10 is a perspective view illustrating a robot in a potential biohazard.

FIG. 10 illustrates a robot 100 that has detected a potential biohazard 1002. According to one embodiment, the robot 100 automatically halts movement upon detection of the biohazard 1002. The robot 100 may be exposed to biohazards 1002 in the form of liquids on the hospital floor such as blood, urine, or other fluids. To avoid spreading such a contamination throughout the healthcare facility, the robot 100 may be equipped with a sensor to detect a liquid or chemical. In one embodiment, this sensor may be a lightweight, flexible sensor that protrudes from the base 102 of the robot 100, and grazes the floor. In another embodiment, the robot 100 may have a chemical sensor that extends from the robot 100 and detects or confirms the detection of the biohazard 1002. The sensor may include a moisture sensor. In yet another embodiment, the robot may employ computer vision, image analysis, or scene analysis techniques to identify a spill, puddle, or other object or substance that is not a part of the floor. In this case the robot 100 may send an alert or notification to the appropriate personnel but navigate around the hazard and continue its current mission.

When the biohazard detection component 214 detects a biohazard, the robot 100 may stop immediately. After the robot 100 stops, it may turn on a signal to alert healthcare facility staff. In another embodiment, the display interface 108 may flash a "Biohazard Detected" message with a biohazard symbol 1004. This message may also be present with options that the healthcare facility staff could select such as, "Resume," "Shut Down," and "Wait." In another embodiment, the robot 100 may send a short message service (SMS) message (or other electronic message) to hospital maintenance or to the manufacturer's tech support department to alert them of the biohazard 1002. In another embodiment, the healthcare facility and/or the robot 100 may be equipped with sterilization pads. The robot 100 may utilize a sterilization pad to perform an auto clean to destroy the biohazard 1002 and sterilize the area. In some embodiments, the sterilization pad may be placed adjacent to a re-lubrication pad, in case the sterilization effort removes the robot 100 wheel lubrication. In other embodiments, a drying pad may also be utilized.

Some of the components that can be used with embodiments disclosed herein are already available, such as general-purpose computers, mobile phones, computer programming tools and techniques, digital storage media, and communications networks. A computing device, such as a laptop, tablet computer, desktop computer, server, Smartphone, or the like, may include a processor, such as a microprocessor, microcontroller, logic circuitry, or the like. The processor may include a special purpose processing device such as an ASIC, PAL, PLA, PLD, FPGA, or other customized or programmable device. The computing device may also include a computer-readable storage device such as non-volatile memory, static RAM, dynamic RAM, ROM, CD-ROM, disk, tape, magnetic, optical, flash memory, or other computer-readable storage medium.

Various aspects of certain embodiments may be implemented using hardware, software, firmware, or a combination thereof. As used herein, a software component may include any type of computer instruction or computer executable code located within or on a non-transitory computer-readable storage medium. A software component may, for instance, comprise one or more physical or logical blocks of computer instructions, which may be organized as a routine, program, object, component, data structure, etc., which performs one or more tasks or implements particular abstract data types.

In certain embodiments, a particular software component may comprise disparate instructions stored in different locations of a computer-readable storage medium, which together implement the described functionality of the component. Indeed, a component may comprise a single instruction or many instructions, and may be distributed over several different code segments, among different programs, and across several computer-readable storage media. Some embodiments may be practiced in a distributed computing environment where tasks are performed by a remote processing device linked through a communications network.

The systems and methods disclosed herein are not inherently related to any particular computer or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network.

Software embodiments may be implemented as a computer program product that comprises a non-transitory storage medium configured to store computer programs and instructions that, when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a Bernoulli drive, a magnetic disk, a punch card, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing the processes, apparatuses, and system described herein. Accordingly, the present embodiments are to be considered illustrative and not restrictive, and the invention is not to be limited to the details given herein, but may be modified within the scope and equivalents of the appended claims.

As used herein, the terms "comprises," "comprising," and any other variation thereof, are intended to cover a non-exclusive inclusion, such that a process, a method, a system, an article, or an apparatus that comprises a list of elements does not include only those elements but may include other elements not expressly listed or inherent to such process, method, system, article, or apparatus.

It will be obvious to those having skill in the art that many changes may be made to the details of the above-described embodiments without departing from the underlying principles of the invention. The scope of the present invention should, therefore, be determined only by the following claims.

What is claimed is:

1. A telepresence robot comprising:
   a drive system configured to move the telepresence robot;
   a control system configured to control the drive system to drive the telepresence robot around a work area;
   an object detection system configured to determine whether a first object encountered by the telepresence robot is a human;
   a status determination system to determine whether the first object is involved in an emergency based on at least one of:
      the first object is approaching the telepresence robot at a velocity that exceeds a predetermined threshold; or
      the first object includes at least one of a transmitter or lights that indicate the first object is involved in the emergency; and
   a social behaviors component configured to instruct to the control system to cause the telepresence robot to maintain a first distance from the first object if the first object is involved in the emergency and a second distance from the first object if the first object is not involved in the emergency, wherein the second distance is greater than the first distance.

2. The telepresence robot of claim 1, wherein the predetermined threshold is lower in a first portion of the work area and higher in a second portion of the work area.

3. The telepresence robot of claim 2, wherein the work area is a hospital, and the first portion is an emergency department of the hospital.

4. The telepresence robot of claim 1, wherein the predetermined threshold comprises a normal velocity for people in a given work area.

5. The telepresence robot of claim 1, wherein the first object comprises a gurney.

6. The telepresence robot of claim 1, wherein the work area comprises a hallway, and wherein the social behaviors component, when the first object is involved in the emergency, is configured to instruct to the control system to cause the telepresence robot to move to a side of the hallway until the first object has passed.

7. The telepresence robot of claim 1, wherein the work area comprises a high-traffic area, and wherein the social behaviors component, when the first object is involved in the emergency, is configured to instruct the control system to cause the telepresence robot to move out of the high-traffic area.

8. The telepresence robot of claim 1, wherein the social behaviors component, when the human is involved in the emergency, is configured to instruct to the control system to cause the telepresence robot to avoid the human.

9. The telepresence robot of claim 1, wherein the telepresence robot is moving along a first path, and wherein the social behaviors component, when the first object is involved in the emergency, is configured to instruct to the control system to cause the telepresence robot to move along a second path.

10. The telepresence robot of claim 9, wherein the social behaviors component, when the first object is involved in the emergency, is configured to instruct to the control system to cause the telepresence robot to move along the second path for a predetermined time or until conditions indicative of the emergency have passed.

11. The telepresence robot of claim 9, wherein the social behaviors component, when the first object is involved in the emergency, is configured to instruct to the control system to cause the telepresence robot avoid high-traffic areas.

12. The telepresence robot of claim 1, wherein the first object is a human, and wherein the social behaviors component, when the telepresence robot being involved in the emergency or having an urgent status, is configured to instruct to the control system to cause the telepresence robot to maintain a closer distance to the human than if the telepresence robot is not involved in the emergency or does not have the urgent status.

13. The telepresence robot of claim 1, wherein the first object is a human, and wherein the social behaviors component is configured to cause the telepresence robot to follow a set of rules when in proximity to one or more humans, and wherein the social behaviors component, when the telepresence robot being involved in the emergency or having an urgent status, the social behaviors component is configured to cause the telepresence robot to violate one or more of the set of rules.

14. The telepresence robot of claim 13, wherein the set of rules include at least one of a rule for a minimum distance for approaching humans, a rule prohibiting the telepresence robot from moving between humans involved in a conversation, or a rule setting a lock-out radius around objects.

* * * * *